United States Patent [19]

Boeckx et al.

[11] Patent Number: 4,767,760

[45] Date of Patent: Aug. 30, 1988

[54] ANTI-PROTOZOAL 5,6-DIHYDRO-2-(SUBSTITUTED PHENYL)-1,2,4-TRIAZINE-3,5(2H,4H)-DIONE DERIVATIVES, COMPOSITIONS, AND METHOD OF USE THEREFOR

[75] Inventors: Gustaaf M. Boeckx, Oud-Turnhout; Alfons H. M. Raeymaekers, Beerse; Victor Sipido, Merksem, all of Belgium

[73] Assignee: Janssen Pharmacuetica N.V., Beerse, Belgium

[21] Appl. No.: 5,550

[22] Filed: Jan. 21, 1987

[30] Foreign Application Priority Data

Jan. 30, 1986 [GB] United Kingdom ............... 8602342

[51] Int. Cl.$^4$ ............... A61K 31/53; C07D 253/06

[52] U.S. Cl. ............... 514/242; 544/182; 544/221; 558/394; 558/404; 558/406

[58] Field of Search ............... 544/182, 221; 514/242; 558/394, 404, 406

[56] References Cited

U.S. PATENT DOCUMENTS 3,905,971 9/1975 Miller ............... 544/182

Primary Examiner—Mary C. Lee
Assistant Examiner—J. G. Mullins
Attorney, Agent, or Firm—Geoffrey G. Dellenbaugh

[57] ABSTRACT

Novel 5,6-dihydro-2-(substituted phenyl)-1,2,4-triazine-3,5(2H,4H)-diones which are effective in destroying or preventing the growth of Protozoa in subjects suffering from such Protozoa.

15 Claims, No Drawings

ANTI-PROTOZOAL 5,6-DIHYDRO-2-(SUBSTITUTED PHENYL)-1,2,4-TRIAZINE-3,5(2H,4H)-DIONE DERIVATIVES, COMPOSITIONS, AND METHOD OF USE THEREFOR

BACKGROUND OF THE INVENTION

2-Phenyl-as-triazine-3,5(2H,4H)-diones and their use for controlling coccidiosis have been described in U.S. Pat. No. 3,912,723. The phenyl moiety in the said triazines may, inter alia, be substituted with a benzoyl-, an α-hydroxy-phenylmethyl- and a phenylsulfonyl radical.

Substituted 2-phenyl-hexahydro-1,2,4-triazine-3,5-diones and their use for combatting Protozoa have been disclosed in Published Eur. Pat. Application No. 0,154,885.

The 5,6-dihydro-2-phenyl-1,2,4-triazine-3,5(2H,4H)-diones, described in the present application, differ from the hereinabove-mentioned triazinones, by the specific substitution of the 2-phenyl moiety, resulting in 5,6-dihydro-1,2,4-triazine-3,5(2H,4H)-diones which are very effective in destroying or preventing the growth of Protozoa in subjects suffering from such Protozoa.

DESCRIPTION OF THE PREFERRED EMBODIMENTS

The present invention is related with 5,6-dihydro-2-(substituted-phenyl)-1,2,4-triazine-3,5(2H,4H)-diones having the formula

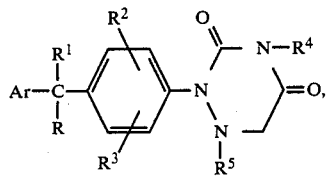

the pharmaceutically acceptable acid addition, metal or amine substitution salts, and stereochemically isomeric forms thereof, wherein:

Ar is thienyl, halo substituted thienyl, naphthalenyl or a radical of formula

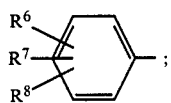

R is hydrogen, $C_{1-6}$ alkyl, cyclo $C_{3-6}$ alkyl, aryl or (aryl)$C_{1-6}$ alkyl;

$R^1$ is cyano or a radical of formula —C(=X)—Y—$R^9$; said

X being O or S,

Y being O, S, $NR^{10}$ or a direct bond;

$R^9$ being hydrogen, aryl, $C_{3-6}$ cycloalkyl or $C_{1-6}$ alkyl optionally substituted with aryl, hydroxy, amino, mono- and di($C_{1-6}$ alkyl)amino, piperidinyl, pyrrolidinyl, 4-morpholinyl, piperazinyl, 4-($C_{1-6}$ alkyl)-piperazinyl, 4-($C_{1-6}$ alkyl-carbonyl)-piperazinyl, 4-($C_{1-6}$ alkyloxycarbonyl)-piperazinyl or 4-((aryl)$C_{1-6}$ alkyl)-piperazinyl; and where Y is a direct bond, $R^9$ may also be halo;

$R^{10}$ is hydrogen, $C_{1-6}$ alkyl or (aryl)$C_{1-6}$alkyl; or $R^9$ and $R^{10}$ taken together with the nitrogen atom bearing said $R^9$ and $R^{10}$ may form a piperidinyl, pyrrolidinyl, 4-morpholinyl, piperazinyl, 4-($C_{1-6}$ alkyl)piperazinyl, 4-($C_{1-6}$alkylcarbonyl)-piperazinyl, 4-($C_{1-6}$alkyloxycarbonyl)-piperazinyl or a 4-((aryl)$C_{1-6}$ alkyl)-piperazinyl radical;

$R^2$, $R^3$, $R^6$, $R^7$ and $R^8$ are each independently hydrogen, halo, trifluoromethyl, $C_{1-6}$ alkyl, hydroxy, $C_{1-6}$ alkyloxy, $C_{1-6}$ alkylcarbonyloxy, mercapto, $C_{1-6}$ alkylthio, $C_{1-6}$ alkylsulfonyl, $C_{1-6}$ alkylsulfinyl, (trifluoromethyl)-sulfonyl, cyano, nitro, amino, mono- and di($C_{1-6}$ alkyl)amino, or ($C_{1-6}$ alkylcarbonyl)amino;

$R^4$ and $R^5$ are each independently hydrogen, aryl, cyclo $C_{3-6}$ alkyl, $C_{2-6}$ alkenyl, $C_{2-6}$ alkynyl, (aryl)$C_{2-6}$ alkenyl or $C_{1-6}$ alkyl optionally substituted with aryl, hydroxy, amino, mono- and di($C_{1-6}$ alkyl)amino, piperidinyl, pyrrolidinyl, 4-morpholinyl, piperazinyl, 4-($C_{1-6}$ alkyl)-piperazinyl, 4-($C_{1-6}$ alkylcarbonyl)-piperazinyl, 4-($C_{1-6}$ alkyloxy-carbonyl)-piperazinyl or 4-((aryl)$C_{1-6}$ alkyl)-piperazinyl;

and $R^5$ may also be $C_{1-6}$ alkylcarbonyl, $C_{1-6}$ alkyloxycarbonyl, (aryl)$C_{1-6}$alkyloxycarbonyl or (aryl)carbonyl;

wherein aryl is phenyl, optionally substituted with up two 3 substituents each independently selected from the group consisting of halo, $C_{1-6}$ alkyl, $C_{1-6}$alkyloxy, trifluoromethyl, hydroxy, mercapto, $C_{1-6}$ alkylthio, $C_{1-6}$alkylsulfonyl, $C_{1-6}$alkylsulfinyl, trifluoromethylsulfonyl, cyano, nitro, amino, mono- and di($C_{1-6}$alkyl)amino and ($C_{1-6}$ alkylcarbonyl)amino.

In the foregoing definitions the term "halo" is generic to fluoro, chloro, bromo and iodo; "$C_{1-6}$ alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; "cyclo $C_{3-6}$ alkyl" embraces cyclopropyl, cyclobutyl, cyclopentyl and cyclohexyl; "$C_{2-6}$ alkenyl" is meant to include straight and branch chained hydrocarbon radicals containing one double bond and having from 2 to 6 carbon atoms such as, for example, ethenyl, 3-propenyl, 2-butenyl and the like; "$C_{2-6}$ alkynyl" is meant to include straight and branch chained hydrocarbon radicals containing one triple bond and having from 2 to 6 carbon atoms such as, for example, ethynyl, 3-propynyl, 2-butynyl and the like.

Preferred compounds within the invention are those wherein Ar is halothienyl or a radical of formula (a) wherein $R^6$ and $R^7$ are, each independently, hydrogen, halo, trifluoromethyl, $C_{1-6}$ alkyloxy, hydroxy or $C_{1-6}$ alkyl; $R^8$ is hydrogen; R is hydrogen, $C_{1-6}$ alkyl, phenyl or halophenyl; $R^2$ and $R^3$ are, each independently, hydrogen, halo, trifluoromethyl or $C_{1-6}$ alkyl; and $R^4$ is hydrogen or $C_{1-6}$ alkyl.

Particularly preferred compounds within the invention are those preferred compounds wherein Ar is a radical of formula (a) wherein $R^6$ is halo, $R^7$ and $R^8$ are hydrogen, R is hydrogen or $C_{1-6}$ alkyl, $R^2$ and $R^3$ independently are halo or hydrogen.

More particularly preferred compounds within the invention are those particularly preferred compounds wherein $R^6$ is 4-chloro, R is hydrogen, $R^2$ is 2-chloro, $R^3$ is 6-chloro or hydrogen and $R^4$ is hydrogen.

The most preferred compounds within the invention are 2,6-dichloro-α-(4-chlorophenyl)-4-(3,4,5,6-tetrahydro-3,5-dioxo-1,2,4-triazin-2(1H)-yl)benzeneacetonitrile and 2-chloro-α-(4-chlorophenyl)-4-(3,4,5,6-tetrahydro-3,5-dioxo-1,2,4-triazin-2(1H)-yl)benzeneacetonitrile and the pharmaceutically acceptable acid addition, metal or amine substitution salts thereof.

The compounds of formula (I) may conveniently be prepared by a reduction reaction of the corresponding 1,2,4-triazine-3,5-(2H,4H)-dione of formula (II), or an acid-addition salt, metal or amine substitution salt form thereof, thus preparing a compound of formula (I) wherein $R^5$ is hydrogen, said compounds being represented by the formula (I-a), and if desired, subsequently reacting the compounds of formula (I-a) with a reagent $R^{5-a}$-W (III), thus preparing compounds of formula (I), wherein $R^5$ is other than hydrogen, said compounds being represented by the formula (I-b). In (III) W represents an appropriate reactive leaving group such as, for example, halo, e.g., chloro, bromo or iodo, or a sulfonyloxy group, e.g. methylsulfonyloxy or 4-methylphenyl-sulfonyloxy and $R^{5-a}$ has the previously defined meaning of $R^5$, provided that it is not hydrogen.

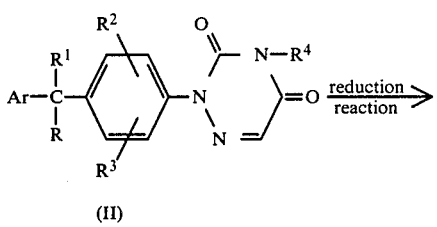

(II)

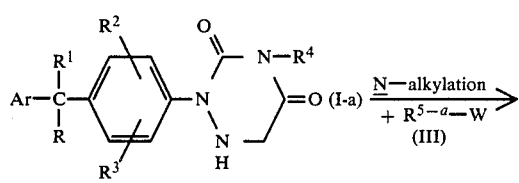

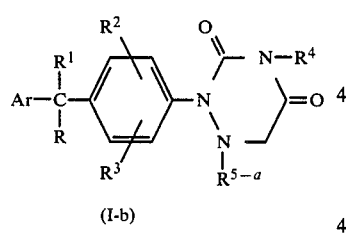

(I-b)

The said reduction reaction is conveniently conducted following art-known procedures for converting a 1,2,4-triazine-3,5-(2H,4H)-dione into a 5,6-dihydro-1,2,4-triazine-3,5-(2H,4H)-dione moiety. A number of such procedures are described in for example the Published Eur. Pat. Application No. 0,154,885 and the references cited therein.

Said reduction reaction may for example be conducted by contacting the starting material of formula (II) with hydrogen in the presence of an appropriate catalyst such as, for example, Raney-nickel, platinum, palladium, platinum(IV) oxide, and the like. Preferably, said reduction reaction is conducted by reacting the starting material (II) with zinc in acetic acid or tin(II) chloride in hydrochloric acid, optionally in the presence of a reaction-inert organic solvent or mixture of such solvents such as, for example, a lower alkanol, e.g. methanol or ethanol; a hydrocarbon, e.g. methylbenzene or dimethylbenzene; a ketone, e.g. 2-propanone, 1-butanone; an ether, e.g. tetrahydrofuran, 1,2-dimethoxyethane, 1,4-dioxane, an ester, e.g. ethyl acetate; N,N-dimethylformamide, N,N-dimethylacetamide; pyridine; acetic acid. Higher temperatures may be used to enhance the reaction rate.

The alkylation reaction of (I-a) with the reagent $R^{5-a}$-W may be conducted following art-known N-alkylation procedures. The alkylation reaction is conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; and ether, e.g., 1,4-dioxane, 1,1'-oxybisethane, tetrahydrofuran and the like; N,N-dimethylformamide (DMF); N,N-dimethylacetamide (DMA); nitrobenzene; dimethyl sulfoxide (DMSO); 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I) wherein $R^1$ is cyano, said compounds being represented by the formula

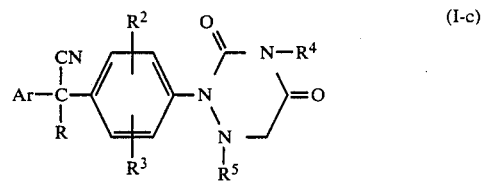

may alternatively be prepared by converting the hydroxy function of a triazinedione of formula

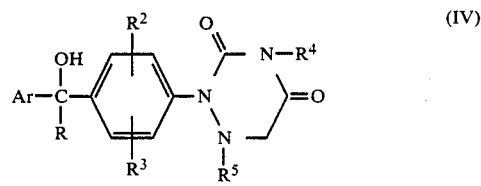

into a nitrile function.

The conversion of (IV) into (I-c) may be effected by art-known procedures. For example, by first converting the hydroxy function into a suitable leaving group and subsequently converting the said leaving group in the thus obtained intermediate having the formula

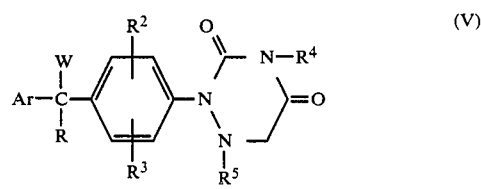

into a nitrile function.

In (V) W has the meaning of an appropriate reactive leaving group such as, for example, halo, e.g., chloro, bromo or iodo, or a sulfonyloxy group, e.g., methylsulfonyloxy or 4-methylphenylsulfonyloxy.

For example, where W represents chloro, the intermediates (V) may be prepared by reacting (IV) with thionyl chloride in a suitable reaction-inert solvent.

The conversion of (V) into (I-c) may be effected, e.g., by reacting (V) with a cyanide, such as, for example, an alkalimetal cyanide, e.g. potassium cyanide, sodium cyanide; copper cyanide; silver cyanide and the like, if desired, in the presence of an appropriate solvent.

The compounds of formula (I) can also be prepared by reacting a 5,6-dihydro-1,2,4-triazine-3,5(2H,4H)-dione having the formula (VII) with a reagent of formula (VI) following art-known procedures for arylating an amine functionality.

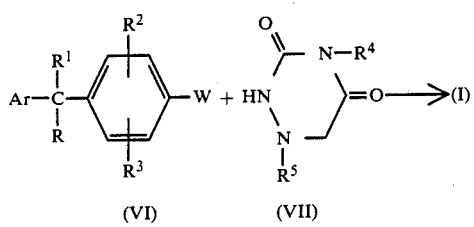

(VI)  (VII)

In (VI) W represents an appropriate reactive leaving group as defined hereinabove and preferably is halo. The reaction of (VI) with (VII) is most conveniently conducted in an appropriate reaction-inert solvent, preferably at higher temperature and in the presence of a suitable base. Suitable reaction inert solvents may, for example, be aromatic hydrocarbons, e.g., benzene, methylbenzene and dimethylbenzene; halogenated hydrocarbons, e.g. trichloromethane and trichloroethane; dipolar aprotic solvents such as N,N-dimethylformamide, N,N-dimethylacetamide, dimethylsulfoxide and the like.

The compounds of formula (I) can also be converted into each other following art-known procedures of functional grouptransformation. Some examples will be cited hereinafter.

In order to simplify the structural representations of the compounds of formula (I) in the schemes illustrating these grouptransformation procedures, the

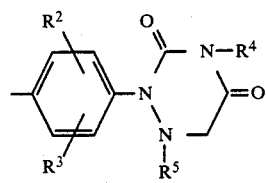

group will hereafter be represented by the symbol D.

For example, the compounds of formula (I) wherein $R^1$ is cyano, said compounds being represented by the formula (I-c) may partially or completely by hydrolysed, thus yielding compounds of formula (I) wherein the radical $R^1$ is a carboxyl or an aminocarbonyl group, the former compound being represented by the formula (I-e), the latter by (I-d). The said partial hydrolysis reaction is preferably conducted in an aqueous acidic medium, e.g. an aqueous sulfuric, hydrochloric or phosphoric acid solution, at room temperature or at slightly increased temperature. Complete hydrolysis is accomplished when increasing either the reaction temperature or the reaction time or both. In the said complete hydrolysis reaction it may be advantageous to add a second acid to the reaction mixture, e.g. acetic acid. In turn, the compounds of formula (I-d) can further by hydrolysed to obtain compounds of formula (I-e) by treating the starting compounds of formula (I-d) with an aqueous acidic solution in the same way as for obtaining (I-e) from (I-c).

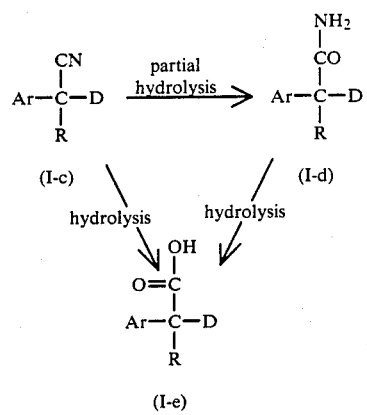

Furthermore, the compounds of formula (I-c) can be converted to the corresponding compounds of formula (I) wherein $R^1$ is an aminothioxomethyl group, said compounds being represented by the formula (I-f), by reacting (I-c) with hydrogen sulfide, preferably in a suitable solvent such as pyridinine, optionally in the presence of an organic base such as a trialkylamine, e.g. triethylamine.

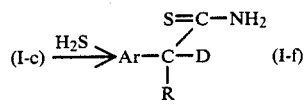

The acids of formula (I-e) can be converted to the corresponding acylhalides of formula (I-g) by treatment with a suitable halogenating agent such as, for example, thionyl chloride, pentachlorophosphorane, sulfuryl chloride. The thus obtained acylhalides of formula (I-g) can further be derivatized to the corresponding amides of formula (I-h) by reacting the starting acylhalide compounds of formula (I-g) with a suitable amine optionally in the presence of an appropriate solvent such as an ether, e.g. tetrahydrofuran, acetonitrile, trichloromethane or dichloromethane.

Or, the said acylhalides of formula (I-g) can conveniently be converted to the corresponding aryl or alkyl ketones of formula (I-i), respectively (I-j), by reacting (I-g) with benzene or substituted benzene in the presence of a Lewis acid catalyst such as aluminum chloride, respectively with an metal alkyl, e.g. methyl lithium, butyl lithium, optionally in the presence of a suitable catalyst, e.g. copper(I) iodide, or with a complex metal alkyl, in a suitable solvent, e.g. tetrahydrofuran.

The acylhalides of formula (I-g) can further be converted to the corresponding esters of formula (I-k) by a suitable alcoholysis reaction. Or, the acids of formula (I-f) can be esterified following art-known procedures, e.g. by treating the starting acids with a alkylhalide in a suitable solvent in the presence of a base, e.g. in N,N-dimethylformamide or N,N-dimethylacetamide in the presence of an alkalimetal carbonate, or by reacting (I-g) with the appropriate alcohol in the presence of a reagent capable of forming an ester functionality e.g. N,N'-methanetetraylbis[cyclohexanamine].

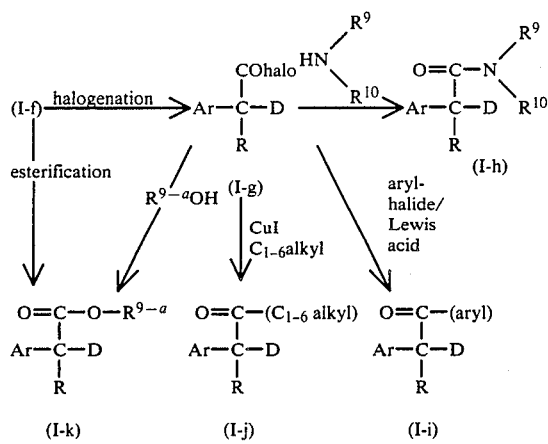

The compounds of formula (I), wherein either $R^4$ or $R^5$ is hydrogen may be converted to the compounds of formula (I) having an $R^4$ and/or $R^5$ other than hydrogen by N-alkylating or N-acylating the starting compounds following art-known procedures, e.g. following the same procedures as described hereinabove for the preparation of (I-b) starting from (I-a).

The compounds of formula (I) which contain an Ar moiety which is a phenyl radical substituted with one or more alkyloxy radicals may be converted to the corresponding alkylcarbonyloxy compounds by treating the starting compounds with an alkanoic acid in the presence of anhydrous hydrohalic acid, e.g. hydrobromic acid in acetic acid. The said alkylcarbonyloxy compounds can in turn be converted to the corresponding hydroxyphenyl compounds by a suitable hydrolysis reaction, e.g. by treatment with an aqueous hydrohalic solution.

A number of intermediates and starting materials in the foregoing preparations are known compounds which may be prepared according to art-known methodologies of preparing said or similar compounds and others are new. A number of such preparation methods will be described hereinafter in more detail.

Several of the intermediates of formula (II) are known compounds and their synthesis is described in the Published Eur. Pat. Application No. 0,170,316.

They may generally be prepared by cyclizing an intermediate of formula

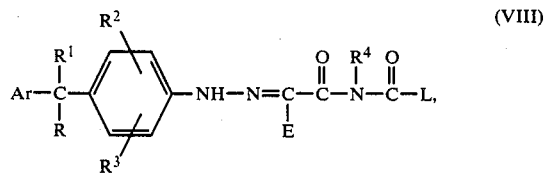

and eliminating the group E of the thus obtained dione

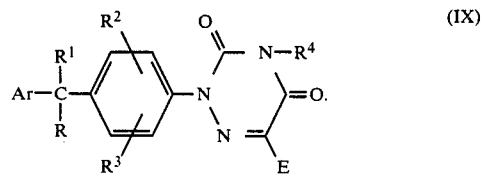

In the intermediates (VIII) L has the meaning of an appropriate leaving group such as $C_{1-6}$ alkyloxy, halo and the like. The group E, as described in the intermediate (VIII) and the triazinedione (IX), represents an appropriate electron attracting group which may conveniently be eliminated from the dione (IX) such as, for example, a carboxyl, a sulfonyloxy, a sulfinyloxy group or a precursor and/or derivative thereof, e.g. an ester, an amide, a cyanide, a $C_{1-6}$ alkylsulfonyloxy, phenylsulfonyloxy, $C_{1-6}$ alkylphenylsulfonyloxy and halophenylsulfonyloxy and the like like groups.

A particularly suitable process for preparing intermediates of formula (II) consists of cyclizing an intermediate of formula (VIII-a) and eliminating the $E^1$ functionality in the thus obtained intermediate of formula (IX-a). In (VIII-a) and (IX-a) $E^1$ represents a cyano, $C_{1-6}$ alkyloxycarbonyl or amido group.

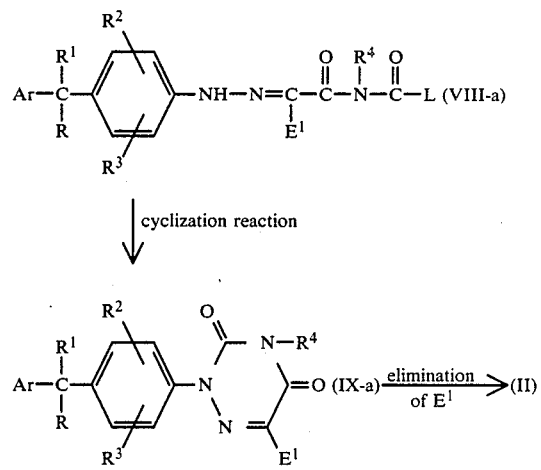

The cyclization reaction may be effected following art-known cyclization procedures as described, for example, in Monatshefte der Chemie, 94, 258–262 (1963), e.g. by heating the starting compound of formula (VIII-a) over its melting point, or by refluxing a mixture of (VIII-a) with a suitable solvent such as, for example, an aromatic hydrocarbon, e.g. benzene, methylbenzene, or dimethylbenzene, an acid, e.g. acetic acid, optionally in the presence of base, e.g. potassium acetate, sodium acetate and the like.

The elimination of the $E^1$ functionality may be effected following art-known procedures as described, for example, in Monatshefte der Chemie, 96, 134–137 (1965), e.g. by converting (IX-a) into a carboxylic acid (X) in a suitable acidic reaction medium such as acetic acid, aqueous hydrochloric acid solutions or mixtures thereof. Elevated temperatures may enhance the rate of the reaction.

The thus obtained carboxylic acids of formula

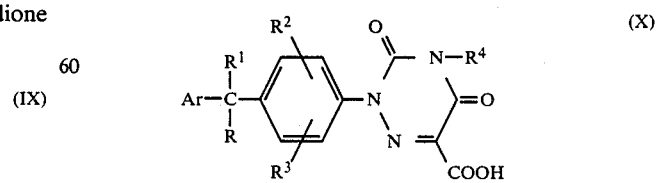

may be converted into an intermediate of formula (II) by art-known decarboxylation reaction procedures, e.g. by heating the carboxylic acid (X) or by heating a solution of (X) in 2-mercaptoacetic acid as described, for example, in U.S. Pat. No. 3,896,124.

The intermediates of formula (VIII) may generally be prepared by reacting a diazonium salt of formula (XI) with a reagent of formula (XII).

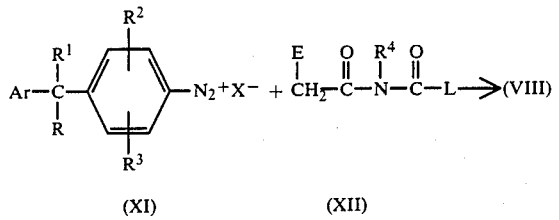

X⁻, described in (XI) has the meaning of an appropriate anion and E and L, as described in (XII), have the previously defined meanings.

The reaction of (XI) with (XII) may conveniently be conducted in a suitable reaction medium as described, for example, in Monatshefte der Chemie, 94, 694–697 (1963). Suitable reaction mediums are, for example, aqueous sodium acetate solutions, pyridine and the like.

The starting diazonium salts (XI) may be derived from a corresponding amine of formula (XIII) following art-known procedures, e.g. by reacting the latter with an alkalimetal or earth alkaline metal nitrite, e.g. sodium nitrite, in a suitable reaction medium.

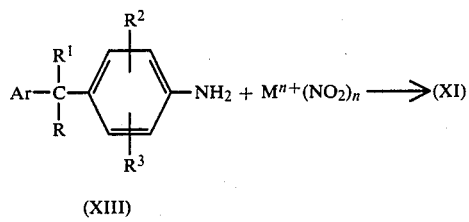

In the hereinabove-described reaction scheme $M^{n+}$ is a alkalimetal or earth alkaline metal kation and n is the integer 1 or 2.

The amines of formula (XIII) may be prepared following procedures analogous to those described in U.S. Pat. No. 4,005,218.

The triazinediones of formula (IV) may conveniently be prepared by reducing the corresponding 1,2,4-triazine-3,5(2$\underline{H}$,4$\underline{H}$)-diones of formula (XIV) following the same procedures as described hereinabove for the preparation of (I) starting from (II) and, if desired, by further N-alkylating the thus obtained triazinedione of formula (IV-a) with a reagent $R^{5-a}$-W (III) following the same procedures described hereinabove for the preparation of (I-b) starting from (I-a).

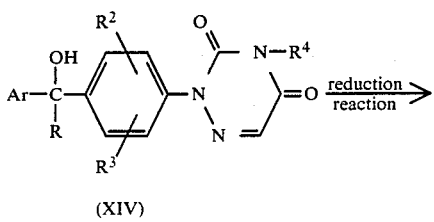

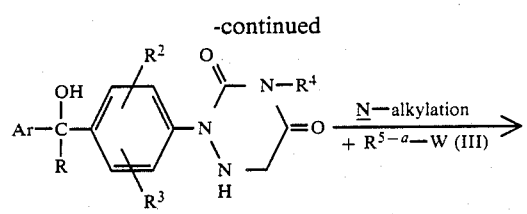

The triazinediones of formula (XIV) may be prepared following the procedures described in U.S. Pat. No. 3,912,723.

The intermediates of formula (II) wherein $R^1$ is cyano, said intermediates being respresented by the formula

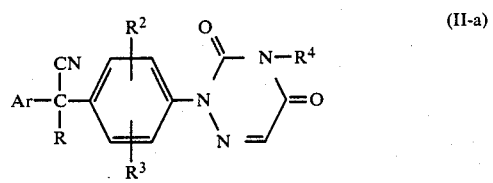

may alternatively be prepared by converting the hydroxy function of a triazinedione of formula

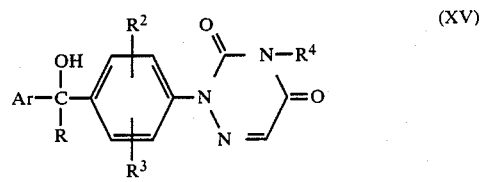

into a nitrile function.

The conversion of (XV) into (II-a) may be effected by art-known procedures. For example, by first converting the hydroxy function into a suitable leaving group and subsequently converting the said leaving group in the thus obtained intermediate having the formula

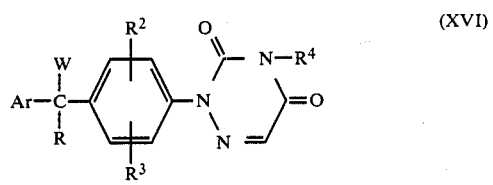

into a nitrile function.

In (XVI) W has the previously defined meaning of an appropriate reactive leaving group.

For example, where W represents chloro, the intermediates (XVI) may be prepared by reacting (XV) with thionyl chloride in a suitable reaction-inert solvent.

The conversion of (XVI) into (II-a) may be effected, e.g., by reacting (XVI) with a cyanide, such as, for example, an alkalimetal cyanide, e.g. potassium cyanide, sodium cyanide; copper cyanide; silver cyanide and the like, if desired, in the presence of an appropriate solvent.

The intermediates of formula (II) may alternatively be prepared by reacting a 1,2,4-triazine-3,5-(2H,4H)-dione of formula (XVII) with an aromatic compound of formula (VI) following the same procedures as described hereinabove for the preparation of (I) starting from (VI) with (VII).

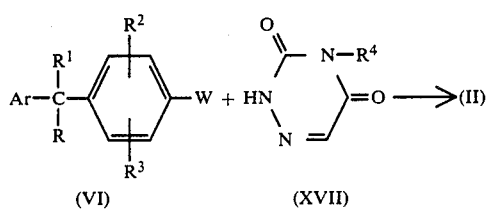

The intermediates of formula (II) can also be converted into each other following art-known procedures of functional groupstransformation. A number of such groupstransformations are represented by the following scheme. In order to simplify the structural representations of the intermediates of formula (II) in these schemes, the

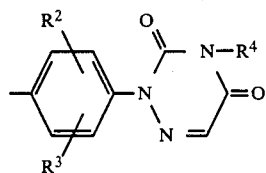

group will hereafter be represented by the symbol D'.

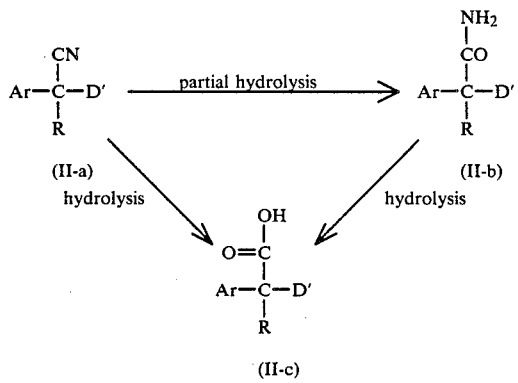

The convertion of (II-a) to (II-b), of (II-a) to (II-c) and of (II-b) to (II-c) can conveniently be done following the same procedures as described hereinabove for the conversion of (I-c) to (I-d), (I-c) to (I-e) and of (I-d) to (I-e).

A further series of such groupstransformations can be represented by the following scheme.

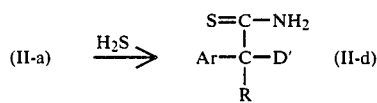

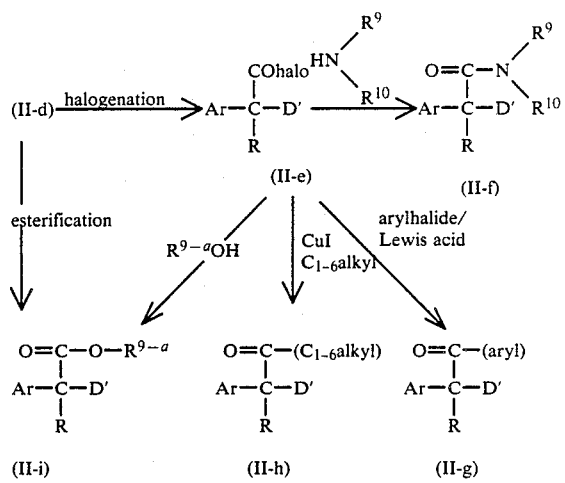

The convertion of (II-a) to (II-d), of (II-d) to (II-e), of (II-e) to (II-f), of (II-d) to (II-i), of (II-e) to (II-i), of (II-e) to (II-h) and of (II-e) to (II-g) can conveniently be done following the same procedures as described hereinabove for the conversion of (I-c) to (I-f), of (I-f) to (I-g), of (I-g) to (I-h), of (I-f) to (I-k), of (I-g) to (I-k), of (I-g) to (I-j) and of (I-g) to I-i).

The intermediates of formula (II), wherein $R^4$ is hydrogen may be converted to the compounds of formula (II) having an $R^4$ other than hydrogen by N-alkylating the starting compounds following art-known procedures, e.g. the procedures described hereinabove for the preparation of (I-b) starting from (I-a).

The intermediates of formula (II) which contain a phenyl radical substituted with one or more alkyloxy radicals may be converted to the corresponding alkylcarbonyloxy compounds which in turn may be converted to the corresponding hydroxyphenyl compounds following the same procedures as described hereinabove for the analogous conversions of the compounds of formula (I).

An additional feature of the present invention comprises the fact that a number of intermediates mentioned in the foregoing preparation schemes are novel compounds.

More particularly, the intermediates of formula (II) wherein $R^1$ is other than cyano, and the intermediates of formula (II) wherein $R^1$ is cyano and in the latter case one of the following conditions is met:

(a) R is other than hydrogen, $C_{1-6}$alkyl, cyclo $C_{3-6}$alkyl or aryl; or (b0) Ar is other than a radical of formula (a) wherein in said radical of formula (a) $R^6$ is other than hydrogen, halo, trifluoromethyl, $C_{1-6}$ alkyl, $C_{1-6}$ alkyloxy, $C_{1-6}$ alkylthio or $C_{1-6}$ alkylsulfonyl; or (c) $R^2$ is other than hydrogen, halo, trifluoromethyl or $C_{1-6}$ alkyl; or (d) $R^4$ is other than hydrogen, said intermediates being represented by the formula

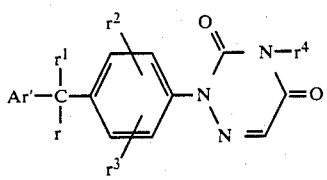

and the pharmaceutically acceptable acid-addition, metal or amine substitution salts, and stereochemically isomeric forms thereof are novel compounds.

Preferred, particularly preferred and more particularly preferred intermediates of formula (II-j) are those of which the preferred, particularly preferred and more particularly preferred compounds of formula (I) can be derived, i.e. those intermediates wherein Ar', r, $r^1$, $r^2$, $r^3$ and $r^4$ are as defined hereinabove for the corresponding radicals Ar, R, $R^1$, $R^2$, $R^3$ and $R^4$ of the preferred, particularly preferred and more particularly preferred compounds of formula (I).

Furthermore, the pharmaceutically acceptable metal or amine substitution salts of those intermediates of formula (II), wherein Ar is a radical of formula (a), and wherein $R^6$, $R^7$ and $R^8$ are each independently hydrogen, halo, trifluoromethyl, $C_{1-6}$ alkyl, $C_{1-6}$ alkyloxy, $C_{1-6}$ alkylthio, or $C_{1-6}$ alkylsulfonyl; $R^2$ and $R^3$ are each independently hydrogen, halo, trifluoromethyl or $C_{1-6}$ alkyl; and wherein $R^1$ is cyano, $R^4$ is hydrogen and wherein R is hydrogen, $C_{1-6}$ alkyl, cyclo $C_{3-6}$ alkyl or phenyl optionally substituted with up to 3 substituents each independently selected from the group consisting of halo, trifluoromethyl, $C_{1-6}$ alkyl, $C_{1-6}$ alkyloxy, $C_{1-6}$ alkylthio and $C_{1-6}$ alkylsulfonyloxy, said compounds being represented by the formula

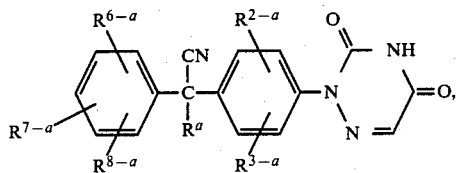

and the stereochemically isomeric forms thereof are also novel compounds.

Preferred are those metal or amine salts of those intermediates of formula (II-k) wherein $R^{6-a}$ is halo and more preferably is chloro, $R^{7-a}$ and $R^{8-a}$ are hydrogen, $R^a$ is hydrogen or $C_{1-6}$ alkyl and more preferably is hydrogen and $R^{2-a}$ and $R^{3-a}$ independently are hydrogen, halo, $C_{1-6}$ alkyl or $C_{1-6}$ alkyloxy and more preferably $R^{2-a}$ is chloro and $R^{3-a}$ is hydrogen or chloro.

Both the intermediates of formula (II-j) and (II-k) are not only novel compounds useful in the preparation of the compounds of formula (I), but they also possess anti-protozoal and more particularly anti-coccidial activity.

The compounds of formula (I) and the intermediates of formula (II) may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely, the salt form can be converted by treatment with alkali into the free base form.

The compounds of formula (I) and the intermediates of formula (II), containing one or more acidic protons, may also be converted to their therapeutically active non-toxic metal or amine substitution salt forms by treatment with appropriate organic or inorganic bases. Appropriate inorganic bases may, for example, be ammonia or bases derived from alkali or earth alkaline metals, e.g. alkali metal or earth alkaline metal oxides or hydroxides such as lithium hydroxide, sodium hydroxide, potassium hydroxide, magnesium hydroxide, calcium hydroxide, calciumoxide and the like; alkalimetal or earth alkaline metal hydrides, e.g. sodium hydride, potassium hydride and the like; alkalimetal hydrogen carbonates or carbonates, e.g. sodium carbonate, potassium carbonate, sodium hydrogen carbonate, calcium carbonate and the like. Appropriate organic bases may, for example be primary, secondary and tertiary aliphatic and aromatic amines such as, for example, methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, N-methylmorpholine, trimethylamine, tripropylamine, quinuclidine, pyridine, quinoline, isoquinoline, diethanolamine and 1,4-diazabicyclo[2,2,2]octane; or quaternary ammonium bases e.g. tetramethylammonium hydroxide, trimethylbenzylammonium hydroxide, triethylbenzylammonium hydroxide, tetraethylammonium hydroxide, and trimethylethylammonium hydroxide.

It is obvious from formulae (I) and (II) that the compounds of the present invention have an asymmetric carbon atom. Consequently, these compounds may exist under two different enantiomeric forms. Pure enantiometic forms of the compounds of formula (I) and the intermediates of formula (II) may be obtained by the application of art-known procedures.

The compounds of formula (I) and the intermediates of formula (II), the pharmaceutically acceptable acid addition salts, metal or amine substitution salts and the possible stereochemically isomeric forms thereof are useful agents in combatting Protozoa. For example, said compounds are found to be active against a wide variety of said Protozoa such as, for example, Sarcodina, Mastigophora, Ciliophora and Sporozoa.

The compounds of formula (I) and the intermediates of formula (II), the pharmaceutically acceptable acid addition salts, metal or amine substitution salts and the possible stereochemically isomeric forms thereof are especially useful agents in combatting Rhizopoda such as, for example, Entamoeba; and Mastigophora such as, for example, Trichomonas, e.g. *Trichomonas vaginalis*, Histomonas, e.g. *Histomonas maleagridis*, and Trypanosoma spp.

In view of their potent activity in combatting Protozoa the compounds of this invention constitute useful tools for the destroying or prevention of the growth of Protozoa and more particularly they can effectively be used in the treatment of subjects suffering from such Protozoa.

In view of the potent activity in combatting Protozoa this invention provides valuable compositions comprising the compounds of formula (I) and the intermediates of formula (II), the acid addition salts, metal or amine substitution salts or possible stereochemically isomeric forms thereof, as the active ingredient in a solvent or a solid, semi-solid or liquid diluent or carrier, and, in addition, it provides an effective method of combatting Protozoa by use of an effective anti-protozoal amount of such compounds of formula (I) and the intermediates of formula (II), or acid addition salts or metal or amine substitution salts thereof. Anti-protozoal compositions comprising an effective amount of an active compound of formula (I) or an active intermediate of formula (II), either alone or in combination with other active therapeutic ingredients, in admixture with suitable carriers may be readily prepared according to conventional pharmaceutical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 10 to about 2000 mg of the active ingredient are preferred.

In view of the anti-protozoal properties of the compounds of formula (I) and the intermediates of formula (II) it is evident that the present invention provides a method of inhibiting and/or eliminating the development of Protozoa in warm-blooded animals suffering from diseases caused by one or more of those Protozoa by the administration of an antiprotozoal effective amount of a compound of formula (I) and intermediates of formula (II), a pharmaceutically acceptable acid addition salt, metal or amine substitution salts or a possible stereochemically isomeric form thereof.

More particularly, in view of their extremely potent activity in combatting Coccidia the compounds of this invention are very useful in the destroying or prevention of the growth of Coccidia in warm-blooded animals. Consequently, the compounds of formula (I) and the intermediates of formula (II), the acid addition salts, metal or amine substitution salts and possible stereochemically isomeric forms thereof are particularly useful anti-coccidial agents as well as coccidiostatics.

Due to their useful anti-coccidial and coccidiostatic activity the subject compounds may be administered in combination with any solid, semi-solid or liquid diluent or carrier as described hereinabove. Additionally, due to their useful coccidiostatic activity the subject compounds may be mixed with any kind of feed supplied to warm-blooded animals although it may also be administered while dissolved or suspended in the drinking water.

The following examples are intended to illustrate and not to limit the scope of the present invention. Unless otherwise stated all parts therein are by weight.

EXAMPLES

(A) Preparation of Intermediates

Example 1

Procedure A

To a stirred mixture of 16 parts of 2-[3-chloro-4-[(2,4-dichlorophenyl)hydroxymethyl]phenyl]-1,2,4-triazine-3,5(2$\underline{H}$,4$\underline{H}$)-dione and 150 parts of trichloromethane are added dropwise, during a period of 5 minutes, 16 parts of thionyl chloride. Upon completion, stirring is continued for 3 hours at reflux temperature. The reaction mixture is evaporated in vacuo. Methylbenzene is added and the whole is evaporated again, yielding 2-[3-chloro-4-[chloro(2,4-dichlorophenyl)methyl]phenyl]-1,2,4-triazine-3,5(2$\underline{H}$,4$\underline{H}$)-dione.

A mixture of 12 parts of 2-[3-chloro-4-[chloro(2,4-dichlorophenyl)methyl]phenyl]-1,2,4-triazine-3,5(2$\underline{H}$,4$\underline{H}$)-dione and 5.4 parts of copper cyanide is stirred and heated first for 3 hours at 130° C. and for 3 hours at 180° C. After cooling, the precipitated product is dissolved in a mixture of trichloromethane and methanol (90:10 by volume). The inorganic precipitate is filtered off and the filtrate is evaporated in vacuo. The residue is purified by column chromatography over silica gel using first a mixture of trichloromethane and acetonitrile (93:7 by volume) as eluent. The pure fractions are collected and the eluent is evaporated. The residue is dissolved in 20 parts of N,N-dimethylformamide and 25 parts of 1,1'-oxybisethane. The product is allowed to crystallize, filtered off and dried, yielding 2-chloro-α-(2,4-dichlorophenyl)-4-(4,5-dihydro-3,5-dioxo-1,2,4-triazin-2(3$\underline{H}$)-yl)benzeneacetonitrile (intermediate 1).

Procedure B

To a stirred mixture of 68 parts of 1-chloro-2-methoxy-4-nitrobenzene, 230 parts of a sodium hydroxide solution 50%, 5 parts of N,N,N-triethylbenzenemethanaminium chloride and 360 parts of tetrahydrofuran is added dropwise, during a 5 minutes period, a solution of 43.2 parts of 4-chlorobenzeneacetonitrile in 90 parts of tetrahydrofuran. Upon completion, stirring is continued for 4 hours at 60° C. The reaction mixture is poured into 2000 parts of crushed ice. The whole is acidified with concentrated hydrochloric acid. The layers are separated. The aqueous phase is extracted with dichloromethane. The combined extracts are dried, filtered and evaporated. The residue is crystallized from 2,2'-oxybispropane. The product is filtered off and dried, yielding α-(4-chlorophenyl)-2-methoxy-4-nitrobenzeneacetonitrile.

A mixture of 8.1 parts of α-(4-chlorophenyl)-2-methoxy-4-nitrobenzeneacetonitrile, 2 parts of a solution of thiophene in methanol 4% and 200 parts of methanol is hydrogenated at normal pressure and at 50° C. with 2 parts of platinum-on-charcoal catalyst 5%. After the calculated amount of hydrogen is taken up, the catalyst is filtered off and the filtrate is evaporated in vacuo. The residue is stirred in a small amount of 2-propanol. The product is filtered off and dried, yielding 4-amino-α-(4-chlorophenyl)-2-methoxybenzeneacetonitrile.

To a stirred and cooled (5°-10° C.) mixture of 5.6 parts of 4-amino-α-(4-chlorophenyl)-2-methoxybenzeneacetonitrile, 6.2 parts of concentrated hydrochloric acid and 50 parts of acetic acid is added dropwise, during a 15 minutes period, a solution of 1.25 parts of sodium nitrite in 10 parts of water at about 10° C. Upon completion, the whole is stirred for 60 minutes and then 3.6 parts of anhydrous sodium acetate and 2.8 parts of ethyl (2-cyanoacetyl)carbamate are added and stirring is continued for 2 hours at room temperature. The reaction mixture is poured into 250 parts of water. The product is filtered off, washed with water and dissolved in a mixture of trichloromethane and methanol (90:10 by volume). The organic layer is dried, filtered and evaporated. The residue is purified by column chromatography over silica gel using a mixture of trichloromethane and methanol (95:5 by volume) as eluent. The pure fractions are collected and the eluent is evaporated in vacuo, yielding ethyl [2-[[4-[(4-chlorophenyl)cyanomethyl]-3-methoxyphenyl]hydrazono]-2-cyanoacetyl]carbamate.

A mixture of 8.3 parts of ethyl [2-[[4-[(4-chlorophenyl)cyanomethyl]-3-methoxyphenyl]hydrazono]-2-cyanoacetyl]carbamate, 1.77 parts of anhydrous potassium acetate and 100 parts of acetic acid is stirred for 2 hours at reflux temperature. The reaction mixture is evaporated in vacuo. The residue is stirred in water. The product is filtered off and dissolved in trichloromethane. The organic layer is dried, filtered and evaporated. The residue is purified by column chromatography over silica gel using a mixture of trichloromethane and methanol (90:10 by volume) as eluent. The pure fractions are collected and the eluent is evaporated in vacuo, yielding 2-[4-[(4-chlorophenyl)cyanomethyl]-3-methoxyphenyl]-2,3,4,5-tetrahydro-3,5-dioxo-1,2,4-triazine-6-carbonitrile.

A mixture of 4 parts of 2-[4-[(4-chlorophenyl)cyanomethyl]-3-methoxyphenyl]-2,3,4,5-tetrahydro-3,5-dioxo-1,2,4-triazine-6-carbonitrile, 24 parts of concentrated hydrochloric acid and 40 parts of acetic acid is stirred and refluxed for 3 hours. The reaction mixture is evaporated in vacuo and the residue is stirred in water. The product is extracted with a mixture of trichloromethane and methanol (90:10 by volume). The extract is dried, filtered and evaporated, yielding 2-[4-[(4-chlorophenyl)cyanomethyl]-3-methoxyphenyl]-2,3,4,5-tetrahydro-3,5-dioxo-1,2,4-triazine-6-carboxylic acid.

A mixture of 4.2 parts of 2-[4-[(4-chlorophenyl)cyanomethyl]-3-methoxyphenyl]-2,3,4,5-tetrahydro-3,5-dioxo-1,2,4-triazine-6-carboxylic acid and 13 parts of 2-mercaptoacetic acid is stirred and heated for 2 hours at 175° C. After cooling, 150 parts of water are added. The aqueous phase is decanted and the remaining oil is stirred in water. The whole is treated with sodium hydrogen carbonate. The product is extracted with a mixture of trichloromethane and methanol (90:10 by volume). The extract is dried, filtered and evaporated. The residue is purified by column chromatography over silica gel using a mixture of trichloromethane and methanol (97:3 by volume) as eluent. The pure fractions are collected and the eluent is evaporated in vacuo. The residue is crystallized from 8 parts of acetonitrile. The product is filtered off, washed with 2,2'-oxybispropane and dried, yielding α-(4-chlorophenyl)-4-(4,5-dihydro-3,5-dioxo-1,2,4-triazin-2(3H)-yl)-3-methoxybenzeneacetonitrile (intermediate 2).

Following the same procedures there are further prepared:

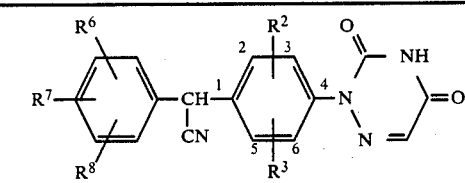

| int. no. | R⁶ | R⁷ | R⁸ | R² | R³ |
|---|---|---|---|---|---|
| 3 | 2-Cl | 4-Cl | 6-Cl | 2-Cl | H |
| 4 | 4-Br | H | H | 2-Cl | H |
| 5 | 4-Br | H | H | 2-Cl | 6-Cl |
| 6 | 4-CH₃COO— | H | H | 2-Cl | 6-Cl |
| 7 | 4-OH | H | H | 2-Cl | 6-Cl |
| 8 | 4-Cl | H | H | 2-OH | H |
| 9 | 4-CH₃S | H | H | 2-Cl | H |
| 10 | 4-CH₃S | H | H | 2-Cl | 6-Cl |

-continued

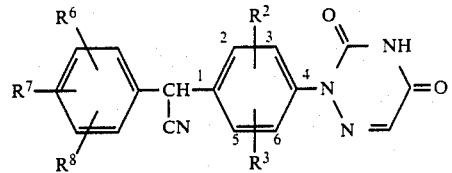

| int. no. | R⁶ | R⁷ | R⁸ | R² | R³ |
|---|---|---|---|---|---|
| 11 | 4-CH₃S | H | H | 2-CH₃ | 6-CH₃ |
| 12 | 4-CH₃S | 3-CH₃ | H | 2-Cl | H |
| 13 | 4-CH₃S | 3-CH₃ | H | 2-Cl | 6-Cl |
| 14 | 4-CH₃SO | H | H | 2-Cl | H |
| 15 | 4-CH₃SO | H | H | 2-Cl | 6-Cl |
| 16 | 4-CH₃SO₂ | H | H | 2-Cl | H |
| 17 | 4-CH₃SO₂ | H | H | 2-Cl | 6-Cl |
| 18 | 4-HS | H | H | 2-Cl | H |
| 19 | 4-HS | H | H | 2-Cl | 6-Cl |

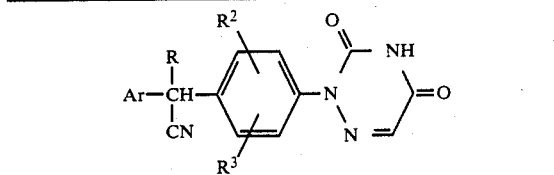

| Comp. | Ar | R | R² | R³ |
|---|---|---|---|---|
| 20 | 2-Cl—5-thienyl | H | Cl | Cl |
| 21 | 2-Cl—5-thienyl | H | Cl | H |
| 22 | 2-Cl—5-thienyl | CH₃ | Cl | Cl |
| 23 | 2-Cl—5-thienyl | CH₃ | Cl | H |
| 24 | 1-naphthalenyl | H | Cl | Cl |
| 25 | 1-naphthalenyl | H | Cl | H |

Example 2

To 30 parts of a sulfuric acid solution in water (90:10 by volume) were added portionwise during a period of 5 minutes 2 parts of 2-chloro-α-(4-chlorophenyl)-4-(4,5-dihydro-3,5-dioxo-1,2,4-triazin-2(3H)-yl)benzeneacetonitrile at room temperature. Upon completion, stirring was continued for 2 hours at 80° C. The reaction mixture was poured into ice water. The product was filtered off, washed with water and purified by column chromatography over silica gel using a mixture of trichloromethane and methanol (95:5 by volume) as eluent. The pure fractions were collected and the eluent was evaporated in vacuo. The residue was stirred in 2,2'-oxybispropane. The product was filtered off and dried, yielding 1.1 parts (54%) of 2-chloro-α-(4-chlorophenyl)-4-(4,5-dihydro-3,5-dioxo-1,2,4-triazin-2(3H)-yl)-benzeneacetamide; mp. 160.7° C. (intermediate 26).

Following the same procedure and using equivalent amounts of the appropriate starting materials, there was also prepared: 2,6-dichloro-α-(4-chlorophenyl)-4-(4,5-dihydro-3,5-dioxo-1,2,4-triazin-2(3H)-yl)benzeneacetamide; mp. 276.4° C. (intermediate 27).

Example 3

To a stirred mixture of 9.2 parts of concentrated sulfuric aid, 5 parts of acetic acid and 5 parts of water were added 1.5 parts of 2-chloro-α-(4-chlorophenyl)-4-(4,5-dihydro-3,5-dioxo-1,2,4-triazin-2(3H)-yl)benzeneacetonitrile at room temperature. The whole was stirred and refluxed for 18 hours. The reaction mixture was poured into 100 parts of ice water. The product was filtered off, washed with water and purified by column chromatography over silica gel using a mixture of trichloromethane, methanol and acetic acid (95:4:1 by volume) as eluent. The pure fractions were collected and the eluent was evaporated in vacuo. The residue was stirred in 2,2'-oxybispropane. The product was filtered off and dried, yielding 0.9 parts (59%) of 2-chloro -α-(4-chlorophenyl)-4-(4,5-dihydro-3,5-dioxo-1,2,4-triazin-2(3H)-yl)benzeneacetic acid; mp. 196.3° C. (intermediate 28).

Example 4

A mixture of 13.2 parts of 2,6-dichloro-α-(4-chlorophenyl)-4-(4,5-dihydro-3,5-dioxo-1,2,4-triazin-2(3H)-yl)benzeneacetamide, 648 parts of concentrated hydrochloric acid and 200 parts of acetic acid was stirred and refluxed for 224 hours. The resulting product was filtered off, washed with water and taken up in 100 parts of water. After treatment with a sodium hydroxide solution, the resulting solution was acidified with concentrated hydrochloric acid. The product was filtered off and purified by column chromatography over silica gel using a mixture of methylbenzene, tetrahydrofuran and acetic acid (70:30:1 by volume) as eluent. The pure fractions were collected and the eluent was evaporated, yielding 3.8 parts (27.8%) of 2,6-dichloro-α-(4-chlorophenyl)-4-(4,5-dihydro-3,5-dioxo-1,2,4-triazin-2(3H)-yl)benzeneacetic acid; mp. 219.5° C. (intermediate 29).

Example 5

A mixture of 6 parts of 2,6-dichloro-α-(4-chlorophenyl)-4-(4,5-dihydro-3,5-dioxo-1,2,4-triazin-2(3H)-yl)benzeneacetonitrile, 1.5 parts of N,N-diethylethanamine and 40 parts of pyridine was stirred at room temperature. Gaseous hydrogen sulfide was bubbled through the mixture during 24 hours. The solvent was evaporated in vacuo and the residue was stirred in water. The precipitated product was filtered off, stirred in 2-propanol and filtered off again. The product was purified by column chromatography over silica gel using a mixture of trichloromethane and methanol (97:3 by volume) as eluent. The pure fractions were collected and the eluent was evaporated in vacuo. The residue was crystallized from 16 parts of acetonitrile. The product was filtered off, washed with 2,2'-oxybispropane and dried, yielding 1.4 parts (21.1%) of 2,6-dichloro-α-(4-chlorophenyl)-4-(4,5-dihydro-3,5-dioxo-1,2,4-triazin-2(3H)-yl)benzeneethanethioamide; mp. 262.7° C. (intermediate 30).

Following the same procedure there is prepared: 2-chloro-α-(4-chlorophenyl)-4-(4,5-dihydro-3,5-1,2,4-triazin-2(3H)-yl)benzeneethanethioamide (intermediate 31).

Example 6

A mixture of 2 parts of 2,6-dichloro-α-(4-chlorophenyl)-4-(4,5-dihydro-3,5-dioxo-1,2,4-triazin-2(3H)-yl)benzeneacetic acid and 48 parts of thionyl chloride was stirred for 1 hour at reflux temperature. The reaction mixture was evaporated, yielding 2.28 parts (100%) of 2,6-dichloro-α-(4-chlorophenyl)-4-(4,5-dihydro-3,5-dioxo-1,2,4-triazin-2(3H)-yl)benzeneacetyl chloride as a residue (intermediate 32).

Following the same procedure there is prepared: 2-chloro-α-(4-chlorophenyl)-4-(4,5-dihydro-3,5-dioxo-1,2,4-triazin-2(3H)-yl)benzeneacetyl chloride (intermediate 33).

Example 7

A mixture of 2.28 parts of 2,6-dichloro-α-(4-chlorophenyl)-4-(4,5-dihydro-3,5-dioxo-1,2,4-triazin-2(3H)-yl)benzeneacetylchloride and 18 parts of piperidine was stirred for 17 hours at room temperature (exothermic reaction). After the addition of water, the solution was acidified with hydrochloric acid. The product was extracted with a mixture of trichloromethane and methanol (95:5 by volume). The extract was dried, filtered and evaporated. The residue was purified by column chromatography over silica gel using a mixture of trichloromethane, methanol and acetic acid (95:4:1 by volume) as eluent. The pure fractions were collected and the eluent was evaporated. The residue was washed with 2,2'-oxybispropane and dried, yielding 1 part (44.0%) of 1-[2-(4-chlorophenyl)-2-[2,6-dichloro-4-(4,5-dihydro-3,5-dioxo-1,2,4-triazin-2(3H)-yl)phenyl]acetyl]piperidine; mp. 216.9° C. (intermediate 34).

Example 8

A mixture of 2.28 parts of 2,6-dichloro-α-(4-chlorophenyl)-4-(4,5-dihydro-3,5-dioxo-1,2,4-triazin-2(3H)-yl)benzeneacetylchloride, 4.5 parts of pyrrolidine and 40 parts of acetonitrile was stirred for 17 hours at room temperature. After evaporation in vacuo, the residue was taken up in water and the mixture was acidified with hydrochloric acid. The product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was dried in vacuo for 48 hours at 110° C., yielding 0.8 parts (36.2%) of 1-[2-(4-chlorophenyl)-2-[2,6-dichloro-4-(4,5-dihydro-3,5-dioxo-1,2,4-triazin-2(3H)-yl)phenyl]acetyl]pyrrolidine; mp. 153.9° C. (intermediate 35).

Example 9

To a stirred mixture of 10 parts of 1-methylpiperazine in 45 parts of tetrahydrofuran was added dropwise a solution of 6.7 parts of 2,6-dichloro-α-(4-chlorophenyl)-4-(4,5-dihydro-3,5-dioxo-1,2,4-triazin-2(3H)-yl)benzeneacetyl chloride in 45 parts of tetrahydrofuran during a period of 5 minutes. Upon complete addition, stirring was continued for 2 hours at room temperature. After evaporation in vacuo, the residue was purified by column chromatography over silica gel using a mixture of trichloromethane and methanol (90:10 by volume) as eluent. The pure fractions were collected and the eluent was evaporated in vacuo. The residue was boiled in acetonitrile. After cooling, the precipitated product was filtered off, washed with 2,2'-oxybispropane and dried, yielding 4.8 parts (62.8%) of 1-[2-(4-chlorophenyl)-2-[2,6-dichloro-4-(4,5-dihydro-3,5-dioxo-1,2,4-triazin-2(3H)-yl)phenyl]acetyl]-4-methylpiperazine; mp. 261.5° C. (intermediate 36).

Following the same procedure there was also prepared: 2,6-dichloro-α-(4-chlorophenyl)-4-(4,5-dihydro-3,5-dioxo-1,2,4-triazin-2(3H)-yl)-N-methylbenzeneacetamide; mp. 278.7° C. (intermediate 37).

Following the same procedure there are further prepared: 2-chloro-α-(4-chlorophenyl)-4-(4,5-dihydro-3,5-dioxo-1,2,4-triazin-2(3H)-yl)-N-methylbenzeneacetamide (intermediate 38). 4-acetyl-1-[2-(4-chlorophenyl)-2-[2-chloro-4-(4,5-dihydro-3,5-dioxo-1,2,4-triazin-2(3H)-yl)phenyl]acetyl]piperazine (intermediate 39).

1-[2-(4-chlorophenyl)-2-[2-chloro-4-(4,5-dihydro-3,5-dioxo-1,2,4-triazin-2(3H)-yl)phenyl]acetyl]-4-(phenylmethyl)piperazine (intermediate 40).

Example 10

A mixture of 4.7 parts of aluminum trichloride and 67.5 parts of benzene was stirred in an ice bath till a temperature of ±10° C. A solution of 4.9 parts of 2,6-dichloro-α-(4-chlorophenyl)-4-(4,5-dihydro-3,5-dioxo-1,2,4-triazin-2(3H)-yl)benzeneacetylchloride in 22.5 parts of benzene was added dropwise during a period of 15 minutes at this low temperature (exothermic reaction). Upon complete addition, stirring was continued for 20 hours at room temperature. The reaction mixture was poured into 500 parts of ice water and the whole was acidified with concentrated hydrochloric acid. The product was extracted with trichloromethane. The extract was dried, filtered and evaporated. The residue was purified by filtration over silica gel using a mixture of trichloromethane and methanol (95:5 by volume) as eluent. The pure fractions were collected and the eluent was evaporated. The residue was further purified three times by column chromatography over silica gel using first a mixture of trichloromethane and methanol (97:3 by volume) and then a mixture of trichloromethane and methanol (99:1 by volume) and finally a mixture of trichloromethane and ethyl acetate (92.5:7.5 by volume) as eluent. The pure fractions were collected and the eluent was evaporated in vacuo. The residue was crystallized from 8 parts of ethanol. The product was filtered off, washed with 2,2'-oxybispropane and dried, yielding 0.7 parts (13.0%) of 2-[3,5-dichloro-4-[1-(4-chlorophenyl)-2-oxo-2-phenylethyl]phenyl]-1,2,4-triazine-3,5(2H,4H)-dione; mp. 143.0° C. (intermediate 41).

Example 11

To a stirred and cooled (−70° C., 2-propanone/CO₂ bath) solution of 5.7 parts of copper(I) iodide in 67.5 parts of tetrahydrofuran were added dropwise 37.5 parts of a methyllithium solution 1.6M in 1,1'-oxybisethane during a period of 15 minutes under nitrogen atmosphere. Upon complete addition, stirring was continued for 30 minutes at this low temperature. A mixture of 4.45 parts of 2,6-dichloro-α-(4-chlorophenyl)-4-(4,5-dihydro-3,5-dioxo-1,2,4-triazin-2(3H)-yl)benzeneacetyl chloride and 22.5 parts of tetrahydrofuran was added dropwise during a period of 30 minutes at −65° C. Upon completion, stirring was continued first for 2 hours at −60° C. and then for 1 hours at −20° C. A saturated ammonium chloride solution in water was added dropwise (exothermic reaction). The precipitate was filtered off and from the filtrate, the organic layer was dried, filtered and evaporated. The residue was purified three times by column chromatography over silica gel: twice using a mixture of trichloromethane and methanol (95:5 and 98:2 by volume) and then a mixture of trichloromethane and ethyl acetate (92.5:7.5 volume) as eluents. The pure fractions were collected and the eluent was evaporated in vacuo. The residue was stirred in acetonitrile. The product was filtered off, washed with 2,2'-oxybispropane and dried, yielding 0.8 parts (18.8%) of 2-[3,5-dichloro-4-[1-(4-chlorophenyl)-2-oxopropyl]phenyl]-1,2,4-triazine-3,5(2H,4H)-dione; mp. 208.4° C. (intermediate 42).

Example 12

A mixture of 5.53 parts of 2,6-dichloro-α-(4-chlorophenyl)-4-(4,5-dihydro-3,5-dioxo-1,2,4-triazin-2(3H)-yl)benzeneacetyl chloride and 160 parts of methanol was stirred for 1 hour at reflux temperature. After evaporation, water was added to the residue and the product was extracted with dichloromethane. The extract was dried, filtered and evaporated. The residue was purified by column chromatography over silica gel using a mixture of trichloromethane, methanol and acetic acid (95:4:1 by volume) as eluent. The pure fractions were collected and the eluent was evaporated. The residue was further purified by column chromatography over silica gel using a mixture of trichloromethane, hexane and methanol (45:45:10 by volume) as eluent. The pure fractions were collected and the eluent was evaporated, yielding 0.9 parts (17.6%) of methyl 2,6-dichloro-α-(4-chlorophenyl)-4-(4,5-dihydro-3,5-dioxo-1,2,4-triazin-2(3H)-yl)benzeneacetate; mp. 121.1° C. (intermediate 43).

Following the same procedure there is also prepared: methyl 2-chloro-α-(4-chlorophenyl)-4-(4,5-dihydro-3,5-dioxo-1,2,4-triazin-2(3H)-yl)benzeneacetate (intermediate 44).

Example 13

To a stirred mixture of 8.5 parts of 2,6-dichloro-α-(4-chlorophenyl)-4-(4,5-dihydro-3,5-dioxo-1,2,4-triazin-2(3H)-yl)benzeneacetic acid, 5.5 parts of potassium carbonate and 45 parts of N,N-dimethylformamide were added 8.52 parts of iodomethane at room temperature. After stirring for 2 hours at 40° C., the reaction mixture was evaporated in vacuo. The residue was stirred in water. The precipitated product was filtered off and dissolved in trichloromethane (the remaining water was separated). The organic layer was dried, filtered and evaporated. The residue was purified by column chromatography over silica gel using a mixture of trichloromethane and methanol (99:1 by volume) as eluent. The pure fractions were collected and the eluent was evaporated in vacuo. The residue was crystallized from acetonitrile. The product was filtered off (the filtrate was set aside) and dried, yielding a first fraction of 1.9 parts (20.9%) of methyl 2,6-dichloro-α-(4-chlorophenyl)-4-(4,5-dihydro-4-methyl-3,5-dioxo-1,2,4-triazin-2(3H)-yl)benzeneacetate. The filtrate, which was set aside (see above), was evaporated in vacuo, yielding a second fraction of 4 parts (44%) of methyl 2,6-dichloro-α-(4-chlorophenyl)-4-(4,5-dihydro-4-methyl-3,5-dioxo-1,2,4-triazin-2(3H)-yl)benzeneacetate as a residue. Total yield: 5.9 parts (64.9%) of methyl 2,6-dichloro-α-(4-chlorophenyl)-4-(4,5-dihydro-4-methyl-B 3,5-dioxo-1,2,4-triazin-2(3H)-yl)benzeneacetate; mp. 173.4° C. (intermediate 45).

Example 14

To a stirred mixture of 4 parts of 2,6-dichloro-α-(4-chlorophenyl)-4-(4,5-dihydro-3,5-dioxo-1,2,4-triazin-2(3H)-yl)benzeneacetonitrile, 1.4 parts of potassium carbonate and 22.5 parts of N,N-dimethylformamide were added 2.84 parts of iodomethane at room temperature. The reaction mixture was stirred for 1.5 hours at 40° C. After evaporation in vacuo, the residue was taken up in water. The precipitated product was filtered off and washed with water. After crystallization from acetonitrile, the product was filtered off, washed with 2,2'-oxybispropane and dried, yielding 2.5 parts (59.2%) of 2,6-dichloro-α-(4-chlorophenyl)-4-(4,5-dihydro-4-methyl-3,5-dioxo-1,2,4-triazin-2(3H)-yl)benzeneacetonitrile; mp. 159.7° C. (intermediate 46).

Following the same procedure there were also prepared:

2,6-dichloro-α-(4-chlorophenyl)-4-[4,5-dihydro-3,5-dioxo-4-(phenylmethyl)-1,2,4-triazin-2(3H)-yl]benzeneacetonitrile; mp. 128.0° C. (intermediate 47);

2,6-dichloro-α-(4-chlorophenyl)-4-(4,5-dihydro-4-methyl-3,5-dioxo-1,2,4-triazin-2(3H)-yl)benzeneacetamide (intermediate 48); and (E)-2,6-dichloro-α-(4-chlorophenyl)-4-[4,5-dihydro-3,5-dioxo-4-(3-phenyl-2-propenyl)-2H-1,2,4-triazin-2-yl]benzeneacetonitrile; mp. 159.2° C. (intermediate 49).

Following the same procedures there are further prepared:

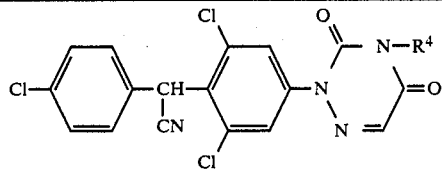

| Int. no. | R⁴ |
|---|---|
| 50 | —C₂H₅ |
| 51 | —C₃H₇—i |
| 52 | —C₄H₉—n |
| 53 | —CH₂—CH=CH |
| 54 | —CH₂—C≡CH |
| 55 | —CH₂CH₂—C₆H₅ |

Example 15

A mixture of 13 parts of 2,6-dichloro-4-(4,5-dihydro-3,5-dioxo-1,2,4-triazin-2(3H)-yl)-α-(4-methoxyphenyl)-benzeneacetonitrile and 300 parts of acetic acid, saturated with hydrogen bromide was stirred for 24 hours at 90° C. The reaction mixture was poured into 500 parts of ice water. The precipitated product was filtered off, washed with water and disolved in trichloromethane. The remaining aqueous layer was removed. The organic layer was dried, filtered and evaporated. The residue was purified by column chromatography over silica gel using a mixture of trichloromethane and ethyl acetate (80:20 by volume) as eluent. The pure fractions were collected and the eluent was evaporated in vacuo. The residue was purified twice by column chromatography over silica gel using a mixture of trichloromethane and ethyl acetate (85:15 by volume) as eluent. The first fraction was collected and the eluent was evaporated. The residue was crystallized from acetonitrile. The product was filtered off, washed with 2,2'-oxybispropane and dried, yielding 2 parts (14.4%) of 4-[cyano[2,6-dichloro-4-(4,5-dihydro-3,5-dioxo-1,2,4-triazin-2(3H)-yl)phenyl]methyl]phenol acetate(ester); mp. 221.5° C. (intermediate 56).

A mixture of 2.3 parts of 4-[cyano[2,6-dichloro-4-(4,5-dihydro-3,5-dioxo-1,2,4-triazin-2(3H)-yl)phenyl]methyl]phenol acetate(ester) and 50 parts of a hydrochloric acid solution 4N was stirred for 4 hours at reflux temperature. The precipitate was filtered off (the filtrate was set aside), washed successively with water, 2-propanol and 2,2'-oxybispropane and dried. The precipitate was combined with the filtrate, which was set aside (see above) and the solvent was evaporated. The residue was stirred and refluxed for 4 hours. After evaporation in vacuo, the residue was dissolved in a mixture of trichloromethane and methanol (90:10 by volume). The solution was dried, filtered and evaporated. The residue was purified by column chromatography over silica gel using a mixture of trichloromethane and methanol (95:5 by volume) as as eluent. The pure fractions were collected and the eluent was evaporated in vacuo. The residue was dissolved in a mixture of acetonitrile and 2,2'-oxybispropane (5:20 by volume). The crystallized product was filtered off and dried, yielding 1 part (48.4%) of 2,6-dichloro-4-(4,5-dihydro-3,5-dioxo-1,2,4-triazin-2(3H)-yl)-α-(4-hydroxyphenyl)benzeneacetonitrile; mp. 209.9° C. (intermediate 57).

Example 16

To a stirred mixture of 5 parts of 2,6-dichloro-α-(4-chlorophenyl)-4-(4,5-dihydro-3,5-dioxo-1,2,4-triazin-2(3H)-yl)benzeneacetonitrile in 40 parts of water were added 5 parts of a solution of 9.6 parts of sodium hydroxide in 100 parts of water under nitrogen atmosphere. The whole was stirred for 10 minutes. The precipitate was filtered off. The product in the filtrate was allowed to crystallize. The product was filtered off, washed with water and dried over weekend at 50° C., yielding 2.4 parts (44.6%) of 2,6-dichloro-α-(4-chlorophenyl)-4-(4,5-dihydro-3,5-dioxo-1,2,4-triazin-2(3H)-yl)benzeneacetonitrile, sodium salt monohydrate; mp. 213.1° C. (intermediate 58).

Following the same procedure and using equivalent amounts of the appropriate starting materials, there was also prepared: 2,6-dichloro-α-(4-chlorophenyl)-4-(4,5-dihydro-3,5-dioxo-1,2,4-triazin-2(3H)benzeneacetonitrile, potassium salt sesquihydrate; mp. 150.7° C. (intermediate 59).

(B) Preparation of Final Compounds

Example 17

To a stirred and refluxed solution of 1.5 parts of 2,6-dichloro-α-(4-chlorophenyl)-4-(4,5-dihydro-3,5-dioxo-1,2,4-triazin2(3H)-yl)benzeneacetic acid in 100 parts of acetic acid were added 3 parts of zinc. Stirring was continued for 30 minutes at reflux temperature. The zinc salts were filtered off and the filtrate was evaporated. The residue was washed with water whereupon the solid product was filtered off and dissolved in a mixture of trichlorometmhane and methanol (90:10 by volume). The solution was dried, filtered and evaporated. The residue was washed with ethyl acetate and 2,2'-oxybispropane and dried, yielding 0.98 parts (67.2%) of 2,6-dichloro-α-(4-chlorophenyl)-4-(3,4,5,6-tetrahydro-3,5-dioxo-1,2,4-triazin-2(1H)-yl)benzeneacetic acid; mp. 194.2° C. (compound 1).

Example 18

To a stirred and refluxed mixture of 1.5 parts of 2-chloro-4-(4,5-dihydro-3,5-dioxo-1,2,4-triazin-2(3H)-yl)-α-(4-fluorophenyl)-α-methylbenzeneacetonitrile and 75 parts of acetic acid were added portionwise 3 parts of zinc during a period of 30 minutes. Upon complete addition, stirring was continued for 3 hours at reflux. The reaction mixture was filtered while hot and the filtrate was concentrated in vacuo to 10 parts of its volume. Water was added to the concentrate. The precipitated product was filtered off and purified by column chromatography over silica gel using a mixture of trichloromethane and methanol (95:5 by volume) as eluent. The pure fractions were collected and the eluent was evaporated in vacuo. The residue was crystallized from acetonitrile. The product was filtered off, washed with 2,2'-oxybispropane and dried, yielding 0.8 parts (53.6%) of 2-chloro-α-(4-fluorophenyl)-α-methyl-4-(3,4,5,6-tetrahydro-3,5-dioxo-1,2,4-triazin-2(1H)-yl)benzeneacetonitrile; mp. 122.5° C. (compound 2).

Example 19

Following the procedures of examples 17 and 18 and using the appropriate starting materials the following compounds are prepared:

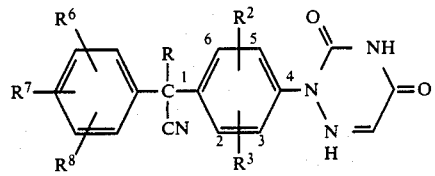

| comp. no. | R¹ | R⁷ | R⁸ | R | R² | R³ | m. p. °C. |
|---|---|---|---|---|---|---|---|
| 3 | H | H | H | CH₃ | H | H | — |
| 4 | 4-Cl | H | H | CH₃ | 2-Cl | H | — |
| 5 | 4-Cl | H | H | CH₃ | 2-CF₃ | H | — |
| 6 | 4-Cl | H | H | 4-Cl—C₆H₄ | 2-Cl | H | — |
| 7 | 4-Cl | H | H | C₃H₇—n | 2-Cl | H | — |
| 8 | 4-Cl | H | H | C₄H₉—n | 2-Cl | H | — |
| 9 | 3-CF₃ | 4-Cl | H | CH₃ | 2-Cl | H | — |
| 10 | 4-Cl | H | H | CH₃ | 2-Cl | 6-Cl | — |
| 11 | 4-Cl | H | H | H | 2-Cl | H | 168.0 |
| 12 | 4-Cl | H | H | CH₃ | 2-Cl | 6-CH₃ | 211.1 |
| 13 | 4-Cl | H | H | CH₃ | 2-Cl | 5-CH₃ | — |
| 14 | 4-Cl | H | H | H | 2-Cl | 6-Cl | 231.2 |
| 15 | 4-Cl | H | H | H | 2-Cl | 6-CH₃ | — |
| 16 | 4-F | H | H | H | 2-Cl | H | — |
| 17 | 4-CH₃ | H | H | H | 2-Cl | H | — |
| 18 | 4-F | H | H | CH₃ | 2-F | H | 165.6 |
| 19 | 4-F | H | H | H | 2-Cl | 6-Cl | — |
| 20 | 4-F | H | H | H | 2-Cl | 6-CH₃ | — |
| 21 | 4-F | H | H | H | 2-CH₃ | 6-CH₃ | — |
| 22 | 4-Cl | H | H | H | 2-CH₃ | 6-CH₃ | — |
| 23 | H | H | H | H | 2-Cl | 6-Cl | — |
| 24 | 4-CH₃O | H | H | H | 2-Cl | 6-Cl | 201.9 |
| 25 | 2-Cl | 4-Cl | H | H | 2-Cl | H | — |
| 26 | 2-Cl | 4-Cl | 6-Cl | H | 2-Cl | H | — |
| 27 | 4-Cl | H | H | H | 2-CH₃O | H | — |
| 28 | 4-Br | H | H | H | 2-Cl | H | — |
| 29 | 4-Br | H | H | H | 2-Cl | 6-Cl | — |
| 30 | 4-CH₃COO | H | H | H | 2-Cl | 6-Cl | — |
| 31 | 4-OH | H | H | H | 2-Cl | 6-Cl | — |
| 32 | 4-Cl | H | H | H | 2-OH | H | — |
| 33 | 4-CH₃S | H | H | H | 2-Cl | H | — |
| 34 | 4-CH₃S | H | H | H | 2-Cl | 6-Cl | — |
| 35 | 4-CH₃S | H | H | H | 2-CH₃ | 6-CH₃ | — |
| 36 | 4-CH₃S | 3-CH₃ | H | H | 2-Cl | H | — |
| 37 | 4-CH₃S | 3-CH₃ | H | H | 2-Cl | 6-Cl | — |
| 38 | 4-CH₃SO₂ | H | H | H | 2-Cl | 6-Cl | — |
| 39 | 4-CH₃SO₂ | H | H | H | 2-Cl | H | — |
| 40 | 4-CH₃S(→O)— | H | H | H | 2-Cl | H | — |
| 41 | 4-CH₃S(→O)— | H | H | H | 2-Cl | 6-Cl | — |
| 42 | 4-HS | H | H | H | 2-Cl | 6-Cl | — |
| 43 | 4-HS | H | H | H | 2-Cl | H | — |

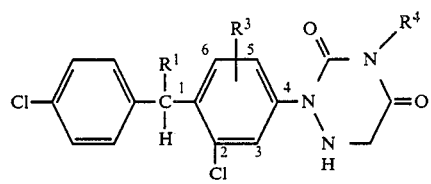

| Comp. | R¹ | R³ | R⁴ | m.p. °C. |
|---|---|---|---|---|
| 44 | CONH—CH₃ | 6-Cl | H | 227.8 |
| 45 | CONH₂ | 6-Cl | H | 247.7 |
| 46 | CO—N(piperazine)N—CH₃ | 6-Cl | H | 192.1 |
| 47 | COOH | H | H | — |
| 48 | CONH₂ | H | H | — |
| 49 | CONH—CH₃ | H | H | — |
| 50 | COOCH₃ | H | H | — |
| 51 | COOCH₃ | 6-Cl | H | — |
| 52 | CSNH₂ | 6-Cl | H | — |
| 53 | CSNH₂ | H | H | — |
| 54 | CO—N(piperidine) | 6-Cl | H | — |
| 55 | CO—N(pyrrolidine) | 6-Cl | H | — |
| 56 | CO—N(piperazine)N—CH₃ | 6-Cl | H | — |
| 57 | CO—N(piperazine)N—CO—CH₃ | 6-Cl | H | — |
| 58 | CO—N(piperazine)N—CH₂C₆H₅ | 6-Cl | H | — |
| 59 | CO—C₆H₅ | 6-Cl | H | 202.5 |
| 60 | CO—CH₃ | 6-Cl | H | — |
| 61 | CN | 6-Cl | CH₃ | oil |
| 62 | CN | 6-Cl | C₂H₅ | — |
| 63 | CN | 6-Cl | C₃H₇—i | — |
| 64 | CN | 6-Cl | C₄H₉—n | — |
| 65 | COOCH₃ | 6-Cl | CH₃ | 123.0 |
| 66 | CO—NH₂ | 6-Cl | CH₃ | 220.9 |
| 67 | CN | 6-Cl | —CH₂—CH=CH | — |
| 68 | CN | 6-Cl | —CH₂—C≡CH | — |
| 69 | CN | 6-Cl | —CH₂—CH=CH—C₆H₅ (E-form) | 175.4 |
| 70 | CN | 6-Cl | —CH₂—C₆H₅ | 186.4 |
| 71 | CN | 6-Cl | —CH₂CH₂—C₆H₅ | |

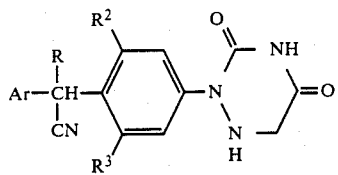

| Comp. | Ar | R | R² | R³ |
| --- | --- | --- | --- | --- |
| 72 | 2-Cl—5-thienyl | H | Cl | Cl |
| 73 | 2-Cl—5-thienyl | H | Cl | H |
| 74 | 2-Cl—5-thienyl | CH₃ | Cl | Cl |
| 75 | 2-Cl—5-thienyl | CH₃ | Cl | H |
| 76 | 1-naphthalenyl | H | Cl | Cl |
| 77 | 1-naphthalenyl | H | Cl | H |

Example 20

A mixture of 4 parts of 2,6-dichloro-α-(4-chlorophenyl)-4-(3,4,5,6-tetrahydro-4-methyl-3,5-dioxo-1,2,4-triazin-2(1H)-yl)benzeneacetonitrile, 12 parts of acetic acid anhydride and 36 parts of methylbenzene was stirred for 90 hours at reflux temperature. After cooling, 16 parts of methanol were added. The solvent was evaporated in vacuo. The residue was stirred in water and the product was extracted with trichloromethane. The extract was dried, filtered and evaporated. The residue was purified by column chromatography over silica gel using trichloromethane as eluent. The pure fractions were collected and the eluent was evaporated. The residue was crystallized for ethanol. The precipitated product was filtered off, washed with 2,2'-oxybispropane and dried, yielding 2.0 parts (42.9%) of 1-acetyl-2-[3,5-dichloro-4-[(4-chlorophenyl)cyanomethyl]phenyl]-1,6-dihydro-4-methyl-1,2,4-triazine-3,5(2H,4H)-dione; mp. 178.1° C. (compound 78).

Example 21

To a stirred mixture of 3 parts of 2,6-dichloro-α-(4-chlorophenyl)-4-(3,4,5,6-tetrahydro-4-methyl-3,5-dioxo-1,2,4-triazin-2(1H)-yl)benzeneacetonitrile and 20 parts of pyridine were added dropwise 1.7 parts of benzoyl chloride during a period of 5 minutes at room temperature and under nitrogen atmosphere. Upon complete addition, stirring was continued overnight at room temperature. The reaction mixture was evaporated in vacuo and the residue was stirred in water. The product was extracted with trichloromethane. The extract was dried, filtered and evaporated. The residue was purified twice by column chromatography over silica gel using trichloromethane as eluent. The pure fractions were collected and the eluent was evaporated in vacuo. The residue was crystallized from 8 parts of acetonitrile. The product was filtered off, washed with 2,2'-oxybispropane and dried, yielding 0.8 parts (20.2%) of 1-benzoyl-2-[3,5-dichloro-4-[(4-chlorophenyl)cyanomethyl]phenyl]-1,6-dihydro-4-methyl-1,2,4-triazine-3,5(2H,4H)-dione; mp. 148.4° C. (compound 79).

Example 22

Following the same procedures of examples 20 and 21 there are further prepared:

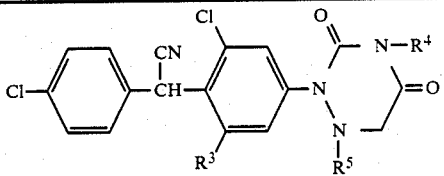

| Comp. | R³ | R⁴ | R⁵ |
| --- | --- | --- | --- |
| 80 | Cl | CH₃ | CH₃ |
| 81 | Cl | CH₂C₆H₅ | CH₂C₆H₅ |
| 82 | H | CH₃ | CO—C₆H₅ |
| 83 | H | CH₃ | CO—CH₃ |
| 84 | Cl | CH₃ | CH₂C₆H₅ |
| 85 | Cl | CH₃ | C₂H₅ |

Example 23

To a stirred mixture of 5 parts of 2-chloro-α-(4-chlorophenyl)-4-(4,5-dihydro-3,5-dioxo-1,2,4-triazin-2(3H)-yl)benzeneacetonitrile in 40 parts of water are added 5 parts of a solution of 9.6 parts of sodium hydroxide in 100 parts of water under nitrogen atmosphere. The whole is stirred for 10 minutes. The precipitate is filtered off. The product in the filtrate is allowed to crystallize. The product is filtered off, washed with water and dried for 48 hours at 50° C., yielding 2-chloro-α-(4-chlorophenyl)-4-(3,4,5,6-tetrahydro-3,5-dioxo-1,2,4-triazin-2(1H)-yl)benzeneacetonitrile, sodium salt; (compound 86).

Following the same procedure and using equivalent amounts of the appropriate starting materials, there was also prepared:

2-chloro-α-(4-chlorophenyl()-4-(3,4,5,6-tetrahydro-3,5-dioxo-1,2,4-triazin-2(1H)-yl)benzeneacetonitrile, potassium salt (compound 87);

2,6-dichloro-α-(4-chlorophenyl)-4-(3,4,5,6-tetrahydro-3,5-dioxo-1,2,4-triazin-2(1H)-yl)benzeneacetonitrile, sodium salt (compound 88);

2,6-dichloro-α-(4-chlorophenyl)-4-(3,4,5,6-tetrahydro-3,5-dioxo-1,2,4-triazin-2(1H)-yl)benzeneacetonitrile, potassium salt (compound 89);

2,6-dichloro-α-(4-chlorophenyl)-4-(3,4,5,6-tetrahydro-3,5-dioxo-1,2,4-triazin-2(1H)-yl(benzeneacetonitrile, ammonium salt (compound 90);

(c) Pharmacological Examples

The strong anti-protozoal activity of the compounds of formula (I) and the intermediates of formula (II), the pharmaceutically acceptable acid addition salts, metal or amine substitution salts and the possible stereochemically isomeric forms thereof is clearly evidenced by the data obtained in the following experiments, which data are only given to illustrate the useful anti-protozoal properties of all the compounds embraced within the invention and not to limit the invention either with respect to the scope of susceptible Protozoa nor with respect to the scope of formula (I) or of formula (II).

Example 13

Outline of anticoccidial efficacy test against *Eimeria tenella*

Hisex chickens were fed with a commercial basal ration not containing a cocciodiostatic agent.

Eighteen-day-old chickens were sorted in groups of two birds. Water was supplied automatically and medicated feed was supplied ad libitum from the day of infection (day 0) until the seventh day (not included) after infection. Unmedicated feed was supplied ad libitum to two groups of four birds for uninfected and infected controls.

Unmedicated feed was a commercial basal ration not containing a coccidiostatic agent. Medicated feed was prepared from unmedicated feed by thoroughly mixing the latter with an amount of the tested compound.

On day 0 the birds were inoculated orally with $10^5$ sporulated oocysts of Eimeria tenella. On day 5 the faecal score was determined and graded:
0 = no blood spots
1 = one or two blood spots
2 = three to five blood spots
3 = more than five blood spots On the seventh day oocyst production is determined by collecting the faces and the oocyst count per gram feces (OPG) and the birds are weighed.

In table 1 the first column shows the average relative weight gain in percent compared with the non-infected controls. The second column shows the average faecal score and the third column illustrates the average oocyst count.

TABLE I

| int./comp. No. | dose of tested compound in ppm in feed | average weight gain | relative faecal score | average oocyst count (OPG) × 1000 |
|---|---|---|---|---|
| int. 27 | 100 | 107 | 0 | 0 |
| int. 29 | 100 | 98 | 0 | 0 |
|  | 10 | 93 | 0.5 | 0 |
| int. 30 | 10 | 104 | 0 | 0 |
| int. 42 | 10 | 102 | 0 | 0 |
| int. 43 | 100 | 96 | 0 | 0 |
|  | 10 | 98 | 0 | 0 |
| int. 46 | 10 | 96 | 0 | 0 |
|  | 1 | 98 | 0.5 | 0 |
| int. 58 | 0.5 | 101 | 0 | 0 |
|  | 0.1 | 100 | 0 | 1 |
| int. 59 | 100 | 98 | 0 | 0 |
|  | 1 | 96 | 0 | 0 |
|  | 0.5 | 97 | 0 | 0 |
| comp. 1 | 10 | 101 | 1 | 0 |
| comp. 2 | 10 | 100 | 0 | 0 |
| comp. 12 | 10 | 95 | 0 | 0 |
| comp. 14 | 10 | 100 | 0 | 0 |
|  | 1 | 100 | 0 | 0 |
|  | 0.1 | 101 | 0 | 0 |
| comp. 18 | 10 | 95 | 0.5 | 0 |
| comp. 24 | 10 | 92 | 0 | 0 |

We claim:
1. A chemical compound having the formula

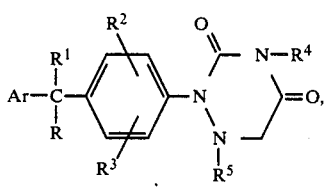

a pharmaceutically acceptable acid-addition, metal or amine substitution salt, or a stereochemically isomeric form thereof, wherein:
Ar is thienyl, halo substituted thienyl, naphthalenyl or a radical of formula

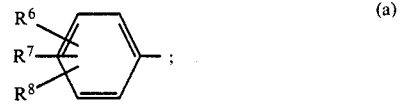

R is hydrogen, $C_{1-6}$ alkyl, cyclo $C_{3-6}$ alkyl, aryl or (aryl)$C_{1-6}$ alkyl;

$R^1$ is cyano or a radical of formula $-C(=X)-Y-R^9$; said
X being O or S,
Y being O, S, $NR^{10}$ or a direct bond;
$R^9$ being hydrogen, aryl, $C_{3-6}$ cycloalkyl or $C_{1-6}$ alkyl optionally substituted with aryl, hydroxy, amino, mono- and di($C_{1-6}$ alkyl)amino, and where Y is a direct bond, $R^9$ may also be halo;
$R^{10}$ is hydrogen, $C_{1-6}$ alkyl or (aryl) $C_{1-6}$ alkyl;
$R^2$, $R^3$, $R^6$, $R^7$ and $R^8$ are each indpendently hydrogen, halo, trifluoromethyl, $C_{1-6}$ alkyl, hydroxy, $C_{1-6}$ alkyloxy. $C_{1-6}$ alkylcarbonyloxy, mercapto, $C_{1-6}$ alkylthio, $C_{1-6}$ alkylsulfonyl, $C_{1-6}$ alkylsulfinyl, (trifluoromethyl)-sulfonyl, cyano, nitro, amino, mono- and di($C_{1-6}$ alkyl)amino, or ($C_{1-6}$ alkylcarbonyl)amino;
$R^4$ and $R^5$ are each independently hydrogen, aryl, cyclo $C_{3-6}$ alkyl, $C_{2-6}$ alkenyl, $C_{2-6}$ alkynyl, (aryl)$C_{2-6}$ alkenyl or $C_{1-6}$ alkyl optionally substituted with aryl, hydroxy, amino, mono- and di($C_{1-6}$ alkyl)amino,
wherein aryl is phenyl, optionally substituted with up two 3 substituents each independently selected from the group consisting of halo, $C_{1-6}$ alkyl, $C_{1-6}$ alkyloxy, trifluoromethyl, hydroxy, mercapto. $C_{1-6}$ alkylthio, $C_{1-6}$ alkylsulfonyl, $C_{1-6}$ alkylsulfinyl, trifluoromethylsulfonyl, cyano, nitro, amino, mono- and di($C_{1-6}$ alkyl)amino and ($C_{1-6}$ alkylcarbonyl)amino.

2. A chemical compound according to claim 1 wherein Ar is halothienyl or a radical of formula (a) wherein $R^6$ and $R^7$ are, each independently, hydrogen, halo, trifluoromethyl, $C_{1-6}$ alkyloxy, hydroxy or $C_{1-6}$ alkyl; $R^8$ is hydrogen; R is hydrogen, $C_{1-6}$ alkyl, phenyl or halophenyl; $R^2$ and $R^3$ are, each independently, hydrogen, halo, trifluoromethyl or $C_{1-6}$ alkyl; and $R^4$ is hydrogen or $C_{1-6}$ alkyl.

3. A chemical compound according to claim 2 wherein Ar is a radical of formula (A) wherein $R^6$ is halo, $R^7$ and $R^8$ are hydrogen, R is hydrogen or $C_{1-6}$ alkyl, $R^2$ and $R^3$ independently are halo or hydrogen.

4. A chemical compound according to claim 3 wherein $R^6$ is 4-chloro, R is hydrogen, $R^2$ is 2-chloro, $R^3$ is 6-chloro or hydrogen and $R^4$ is hydrogen.

5. A chemical compound according to claim 1 wherein the compound is 2,6-dichloro-α-(4-chlorophenyl)-4-(3,4,5,6-tetrahydro-3,5-dioxo-1,2,4-triazin-2(1H)-yl)benzeneacetonitrile or 2-chloro-α-(4-chlorophenyl)-4-(3,4,5,6-tetrahydro-3,5-dioxo-1,2,4-triazin-2(1H)-yl)benzeneacetonitrile.

6. An anti-protozoal composition comprising an inert carrier and an active ingredient an anti-protozoal effective amount of a compound having the formula

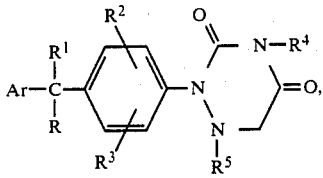

a pharmaceutically acceptable acid-addition, metal or amine substitution salt, or a stereochemically isomeric form thereof, wherein:

Ar is thienyl, halo substituted thienyl, naphthalenyl or a radical of formula

R is hydrogen, $C_{1-6}$ alkyl, cyclo $C_{3-6}$ alkyl, aryl or (aryl)$C_{1-6}$ alkyl;
$R^1$ is cyano or a radical of formula $-C(=X)-Y-R^9$; said
  X being O or S,
  Y being O, S, $NR^{10}$ or a direct bond;
  $R^9$ being hydrogen, aryl, $C_{3-6}$ cycloalkyl or $C_{1-6}$ alkyl optionally substituted with aryl, hydroxy, amino, mono- and di($C_{1-6}$ alkyl)amino, and where Y is a direct bond, $R^9$ may also be halo;
  $R^{10}$ is hydrogen, $C_{1-6}$ alkyl or (aryl) $C_{1-6}$ alkyl;
$R^2$, $R^3$, $R^6$, $R^7$ and $R^8$ are each independently hydrogen, halo, trifluoromethyl, $C_{1-6}$ alkyl, hydroxy, $C_{1-6}$ alkyloxy, $C_{1-6}$ alkylcarbonyloxy, mercapto, $C_{1-6}$ alkylthio, $C_{1-6}$ alkylsulfonyl, $C_{1-6}$ alkylsulfinyl, (trifluoromethyl)-sulfonyl, cyano, nitro, amino, mono- and di($C_{1-6}$ alkyl)amino, or ($C_{1-6}$ alkylcarbonyl)amino;
$R^4$ and $R^5$ are each independently hydrogen, aryl, cyclo $C_{3-6}$ alkyl, $C_{2-6}$ alkenyl, $C_{2-6}$ alkynyl, (aryl)$C_{2-6}$ alkenyl or $C_{1-6}$ alkyl optionally substituted with aryl, hydroxy, amino, mono- and di($C_{1-6}$ alkyl)amino,
and $R^5$ may also be $C_{1-6}$ alkylcarbonyl, $C_{1-6}$ alkyloxycarbonyl, (aryl)$C_{1-6}$ alkyloxycarbonyl or (aryl)carbonyl;
wherein aryl is phenyl, optionally substituted with up two 3 substituents each independently selected from the group consisting of halo, $C_{1-6}$ alkyl, $C_{1-6}$ alkyloxy, trifluoromethyl, hydroxy, mercapto, $C_{1-6}$ alkylthio, $C_{1-6}$ alkylsulfonyl, $C_{1-6}$ alkylsulfinyl, trifluoromethylsulfonyl, cyano, nitro, amino, mono- and di($C_{1-6}$ alkyl)amino and ($C_{1-6}$ alkylcarbonyl)amino.

7. A composition according to claim 6 wherein Ar is halothienyl or a radical of formula (a) wherein $R^6$ and $R^7$ are, each independently, hydrogen, halo, trifluoromethyl, $C_{1-6}$ alkyloxy, hydroxy or $C_{1-6}$ alkyl; $R^8$ is hydrogen; R is hydrogen, $C_{1-6}$ alkyl, phenyl or halophenyl; $R^2$ and $R^3$ are, each independently, hydrogen, halo, trifluoromethyl or $C_{1-6}$ alkyl; and $R^4$ is hydrogen or $C_{1-6}$ alkyl.

8. A composition according to claim 7 wherein Ar is a radical of formula (a) wherein $R^6$ is halo, $R^7$ and $R^8$ are hydrogen, R is hydrogen or $C_{1-6}$ alkyl, $R^2$ and $R^3$ independently are halo or hydrogen.

9. A composition according to claim 8 wherein $R^6$ is 4-chloro, R is hydrogen, $R^2$ is 2-chloro, $R^3$ is 6-chloro or hydrogen and $R^4$ is hydrogen.

10. A composition according to claim 6 wherein the compound is 2,6-dichloro-α-(4-chlorophenyl)-4-(3,4,5,6-tetrahydro-3,5-dioxo-1,2,4-triazin-2(1H)-yl)benzeneacetonitrile or 2-chloro-α-(4-chlorophenyl)-4-(3,4,5,6-tetrahydro-3,5-dioxo-1,2,4-triazin-2(1H)-yl)-benzeneacetonitrile.

11. A method of destroying or preventing the growth of Protozoa in subjects suffering from such Protozoa by the administration of an anti-protozoal effective amount of a compound having the formula

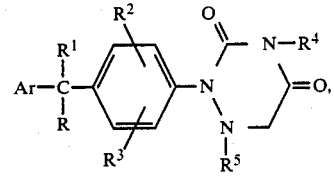

a pharmaceutically acceptable acid-addition, metal or amine subsitution salt, or a stereochemically isomeric form thereof, wherein:

Ar is thienyl, halo substituted thienyl, naphthalenyl or a radical of formula

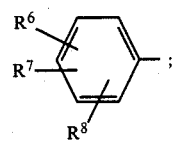

R is hydrogen, $C_{1-6}$ alkyl, cyclo $C_{3-6}$ alkyl, aryl or (aryl)$C_{1-6}$ alkyl;
$R^1$ is cyano or a radical of formula $-C(=X)-Y-R^9$; said
  X being O is S,
  Y being O, S, $NR^{10}$ or a direct bond;
  $R^9$ being hydrogen, aryl, $C_{3-6}$ cycloalkyl or $C_{1-6}$ alkyl optionally substituted with aryl, hydroxy, amino, mono- and di($C_{1-6}$ alkyl)amino, and where Y is a direct bond, $R^9$ may also be halo;
  $R^{10}$ is hydrogen, $C_{1-6}$ alkyl or (aryl) $C_{1-6}$ alkyl;
$R^2$, $R^3$, $R^6$, $R^7$ and $R^8$ are each independently hydrogen, halo, trifluoromethyl, $C_{1-6}$ alkyl, hydroxy, $C_{1-6}$ alkyloxy, $C_{1-6}$ alkylcarboxyloxy, mercapto, $C_{1-6}$ alkylthio, $C_{1-6}$ alkylsulfonyl, $C_{1-6}$ alkylsulfinyl, (trifluoromethyl)-sulfonyl, cyano, nitro, amino, mono- and di($C_{1-6}$ alkyl)amino, or ($C_{1-6}$ alkylcarbonyl)amino;
$R^4$ and $R^5$ are each independently hydrogen, aryl, cyclo $C_{3-6}$ alkyl, $C_{2-6}$ alkenyl, $C_{2-6}$ alkynyl, (aryl)$C_{2-6}$ alkenyl or $C_{1-6}$ alkyl optionally substituted with aryl, hydroxy, amino, mono- and di($C_{1-6}$ alkyl)amino,
and $R^5$ may also be $C_{1-6}$ alkylcarbonyl, $C_{1-6}$ alkyloxycarbonyl, (aryl)$C_{1-6}$ alkyloxycarbonyl or (aryl)carbonyl;
wherein aryl is phenyl, optionally substituted with up two 3 substituents each independently selected from the group consisting of halo, $C_{1-6}$ alkyl, $C_{1-6}$ alkyloxy, trifluoromethyl, hydroxy, mercapto, $C_{1-6}$ alkylthio, $C_{1-6}$ alkylsulfonyl, $C_{1-6}$ alkylsulfinyl, trifluoromethylsulfonyl, cyano, nitro, amino, mono- and di($C_{1-6}$ alkyl)amino and ($C_{1-6}$ alkylcarbonyl)amino.

12. A method according to claim 11 wherein Ar is halothienyl or a radical of formula (a) wherein $R^6$ and $R^7$ are, each independently, hydrogen, halo, trifluoromethyl, $C_{1-6}$ alkyloxy, hydroxy or $C_{1-6}$ alkyl; $R^8$ is hydrogen; R is hydrogen, $C_{1-6}$ alkyl, phenyl or halophenyl; $R^2$ and $R^3$ are, each independently, hydrogen, halo, trifluoromethyl or $C_{1-6}$ alkyl; and $R^4$ is hydrogen or $C_{1-6}$ alkyl.

13. A method according to claim 12 wherein Ar is a radical of formula (a) wherein $R^6$ is halo, $R^7$ and $R^8$ are hydrogen, R is hydrogen or $C_{1-6}$ alkyl, $R^2$ and $R^3$ independently are halo or hydrogen.

14. A method according to claim 13 wherein $R^6$ is 4-chloro, R is hydrogen, $R^2$ is 2-chloro, $R^3$ is 6-chloro or hydrogen and $R^4$ is hydrogen.

15. A method according to claim 11 wherein the compound is 2,6-dichloro-α-(4-chlorophenyl)-4-(3,4,5,6-tetrahydro-3,5-dioxo-1,2,4-triazin-2(1$\underline{H}$)-yl)benzeneacetonitrile or 2-chloro-α-(4-chloro-phenyl)-4-(3,4,5,6-tetrahydro-3,5-dioxo-1,2,4-triazin-2(1$\underline{H}$)-yl)-benzeneacetonitrile.

* * * * *

UNITED STATES PATENT AND TRADEMARK OFFICE
CERTIFICATE OF CORRECTION

PATENT NO. : 4,767,760

DATED : August 30, 1988

INVENTOR(S) : Gustaaf M. Boeckx et al.

It is certified that error appears in the above-identified patent and that said Letters Patent is hereby corrected as shown below:

Claim 1, column 32, line 32, after "amino," (second occurrence) insert --and $R^5$ may also be $C_{1-6}$ alkylcarbonyl, $C_{1-6}$ alkyloxycarbonyl, (aryl) $C_{1-6}$ alkyloxycarbonyl or (aryl) carbonyl;--

Claim 3, column 32, line 52
delete "(A)" and insert --(a)--.

Claim 11, column 34, line 35
delete "is" and insert --or--.

Signed and Sealed this

Twenty-first Day of March, 1989

Attest:

DONALD J. QUIGG

*Attesting Officer*     *Commissioner of Patents and Trademarks*